United States Patent
Von Allmen et al.

(10) Patent No.: US 11,103,210 B2
(45) Date of Patent: Aug. 31, 2021

(54) IMAGE GUIDED AUTONOMOUS NEEDLE INSERTION DEVICE FOR VASCULAR ACCESS

(71) Applicants: Children's Hospital Medical Center, Cincinnati, OH (US); B.G. Negev Technologies and Applications Ltd., Beer-Sheva (IL)

(72) Inventors: Daniel Von Allmen, Cincinnati, OH (US); Hugo Guterman, Be'er Sheva (IL)

(73) Assignees: Children's Hospital Medical Center, Cincinnati, OH (US); B.G. Negev Technologies and Applications Ltd., Beer-Sheva (IL)

( * ) Notice: Subject to any disclaimer, the term of this patent is extended or adjusted under 35 U.S.C. 154(b) by 382 days.

(21) Appl. No.: 15/308,606

(22) PCT Filed: May 20, 2015

(86) PCT No.: PCT/US2015/031754
§ 371 (c)(1),
(2) Date: Nov. 2, 2016

(87) PCT Pub. No.: WO2015/179505
PCT Pub. Date: Nov. 26, 2015

(65) Prior Publication Data
US 2017/0188990 A1    Jul. 6, 2017

Related U.S. Application Data

(60) Provisional application No. 62/001,035, filed on May 20, 2014.

(51) Int. Cl.
*A61B 8/08*    (2006.01)
*A61B 5/15*    (2006.01)
(Continued)

(52) U.S. Cl.
CPC ........ *A61B 8/0841* (2013.01); *A61B 5/15003* (2013.01); *A61B 5/153* (2013.01);
(Continued)

(58) Field of Classification Search
None
See application file for complete search history.

(56) References Cited

U.S. PATENT DOCUMENTS 7,662,128 B2 * 2/2010 Salcudean ............. A61B 10/04
604/117
8,308,741 B2   11/2012 Hyde et al.
(Continued)

FOREIGN PATENT DOCUMENTS

WO   WO 2013/034175 A1   3/2013

OTHER PUBLICATIONS

International Search Report and Written Opinion issued by the ISA/US, Commission for Patents, dated Aug. 19, 2015, for International Application No. PCT/US2015/031754; 11 pages.
(Continued)

*Primary Examiner* — Pascal M Bui Pho
*Assistant Examiner* — Marjan Saboktakin
(74) *Attorney, Agent, or Firm* — Bose McKinney & Evans LLP

(57) ABSTRACT

An image guided autonomous needle insertion device including a delivery system, a path planner, an image processor, and a human machine interface. The system also includes an ultrasound probe in communication with a frame grabber, a percutaneous insertion device, and at least a first actuator for moving the percutaneous insertion device within a first degree of freedom and a second actuator for moving the percutaneous insertion device within a second degree of freedom. Each actuator has a corresponding position sensor for detecting its location with respect to a target. The system
(Continued)

can further comprise an image processor for removing noise and segmenting the ultrasound images to highlight potential targets.

13 Claims, 34 Drawing Sheets

(51) Int. Cl.
    *A61B 5/153*     (2006.01)
    *A61M 5/32*     (2006.01)
    *A61M 5/46*     (2006.01)
    *A61B 8/00*     (2006.01)

(52) U.S. Cl.
    CPC ...... *A61B 5/1535* (2013.01); *A61B 5/150748* (2013.01); *A61B 8/4444* (2013.01); *A61M 5/3287* (2013.01); *A61M 5/46* (2013.01); *A61B 5/15016* (2013.01); *A61B 5/150389* (2013.01); *A61B 5/150503* (2013.01)

(56) References Cited

U.S. PATENT DOCUMENTS

| | | | |
|---|---|---|---|
| 2012/0190981 A1* | 7/2012 | Harris | A61B 34/30 600/439 |
| 2012/0259220 A1 | 10/2012 | Sheldon | |
| 2013/0184572 A1* | 7/2013 | Velusamy | A61B 6/032 600/427 |
| 2014/0107569 A1* | 4/2014 | Fischer | A61M 5/3287 604/95.01 |

OTHER PUBLICATIONS

Examination Report issued by IP Australia, dated Mar. 28, 2019, for Australian Patent Application No. 2015264243; 3 pages.
European Supplementary Search Report and Search Opinion Received for EP Application No. 15796430.5, dated Nov. 27, 2017, 6 pages.
International Preliminary Report on Patentability received for PCT Patent Application No. PCT/US2015/031754, dated Dec. 1, 2016, 10 pages.

* cited by examiner

IMAGE GUIDED AUTONOMOUS NEEDLE INSERTION DEVICE FOR VASCULAR ACCESS

CROSS-REFERENCE TO RELATED APPLICATION

This application is a U.S. National Phase Patent Application based on International Application No. PCT/US2015/031754, filed May 20, 2015, which claims priority to U.S. Provisional Application Ser. No. 62/001,035, filed May 20, 2014, the disclosures of which are expressly incorporated by reference herein.

BACKGROUND AND SUMMARY OF THE DISCLOSURE

The present invention relates to surgical robots and, more particularly, to a system and method of using ultrasound in percutaneous medical procedures, such as needle insertion into a subcutaneous vein.

Percutaneous access to internal lesions is a common and critical aspect in many surgical procedures used in diagnosis and treatment. For procedures performed via an endovascular approach, access to the vascular system must be achieved by cannulation of vessels imaged by ultrasound before any endovascular devices can be introduced. Biopsy of solid organ targets such as suspicious breast lesions, identified on imaging studies require accurate insertion of biopsy needles placed percutaneously.

Current technology generally relies on operator skill and trial and error attempts to correctly position interventional needles even when guided by imaging modalities. Poor placement of a needle tip can result in failure to complete interventions such as those requiring vascular access, false negatives biopsies, imprecise delivery of radiation therapy (such as radioactive seeds implanted during brachytherapy), and ablation of healthy tissue instead of cancerous tissue. Several factors, including errors in insertion location, trajectory, needle bending, and tissue deformation, can lead to poor needle tip placement. When such errors occur in clinical settings, the solution typically involves retraction and reinsertion. In current practice, a clinician typically has limited control over the path of a needle once inserted into the tissue and limited ability to know the precise trajectory required to achieve the desired position of the needle tip.

The accuracy and efficiency with which a needle can be inserted to a specific site within the body has a large impact on the efficiency and efficacy of the procedure itself. The pediatric population is particularly challenging from a vascular access standpoint given the size of the targets. Several techniques have been developed to aid in the process ranging from Doppler tipped needles to free hand ultrasound guidance and all require training and experience yet ultimately rely on the trial and error approach.

An illustrative system using real-time three-dimensional (RT3D) ultrasound in laparoscopic procedures is disclosed in U.S. Patent Application Publication No. 2009/0287223 to Pua et al., the disclosure of which is hereby expressly incorporated by reference herein.

There is a strong desire in current medical therapy to reduce the invasiveness and cost of interventional procedures while increasing the efficiency, accuracy and ease with which they are performed. Many interventions that required open surgical procedures under general anesthesia in the past have evolved into endovascular or percutaneous interventions that can be performed under local anesthesia with minimal morbidity. Considered broadly, the fundamental challenge that is common to all of these interventions involves the ability to accurately access a particular point in the body.

There is a desire to provide a handheld needle delivery device which can be used in any ultrasound (US) system and adapted to any ultrasound probe (UP). This allows the operator to use the system in the same way he/she usually works.

The illustrative image guided autonomous needle insertion device of the present disclosure introduces a needle tip into a target lesion or vessel autonomously thus improving the success rate and reducing the time, cost and experience necessary to achieve vascular access.

According to an illustrative embodiment of the present disclosure, a percutaneously placed device insertion system, illustratively an image guided autonomous needle insertion system, includes an ultrasound probe and a percutaneous insertion device. The percutaneous insertion device includes a frame grabber in communication with the ultrasound probe for capturing ultrasound images from the ultrasound probe, and a dispenser and control unit coupled to the ultrasound probe. The dispenser and control unit includes a percutaneously placed device supported by a holder, a first actuator configured to move the percutaneously placed device within a first degree of freedom, a second actuator configured to move the percutaneously placed device within a second degree of freedom, a first position sensor configured to detect the relative position of the first actuator, and a second position sensor configured to detect the relative position of the second actuator.

An image processor is in communication with the frame grabber and includes an image preprocessing module and an image segmentation module. The image preprocessing module is configured to remove noise from the ultrasound image received from the frame grabber, and to calibrate the ultrasound image. The image segmentation module is configured to decompose the ultrasound image into separate objects.

A path planner is configured to determine a desired path for the percutaneously placed device. The path planner includes a device detection and tracking module, and a target detection and tracking module. The device detection and tracking module is configured to receive information from the first and second position sensors to determine the relative positions of the first and second motors and the anticipated trajectory of the percutaneously placed device. The target detection and tracking module is configured to receive information from the image processor to determine the global position of a target vein.

A human machine interface is in communication with the path planner and includes a plurality of operator inputs. The operator inputs include a first directional input configured to cause the first actuator to move the percutaneously placed device in a first direction within the first degree of freedom, a second directional input configured to cause the first actuator to move the percutaneously placed device in a second direction within the first degree of freedom, a start input configured to cause the second actuator to move the percutaneously placed device in a first direction within the second degree of freedom toward the target vein, and an out input configured to cause the second actuator to move the percutaneously placed device in a second direction within the second degree of freedom away from the target vein.

According to another illustrative embodiment of the present disclosure, an image guided autonomous needle insertion system includes an ultrasound probe, a mount coupled to the ultrasound probe, and a needle assembly supported by the mount and configured to move with the ultrasound probe. The needle assembly includes a needle having first and second degrees of freedom relative to the mount and the ultrasound probe. A first actuator is configured to move the needle within a first degree of freedom, and a second actuator is configured to move the needle within a second degree of freedom. A first position sensor is configured to detect the relative position of the first actuator, and a second position sensor is configured to detect the relative position of the second actuator. A human machine interface is operably coupled to the first and second actuators. The first actuator is configured to rotate the needle assembly about an x-axis extending perpendicular to the needle to align the needle with a target vein. The second actuator is configured to translate the needle assembly along a z-axis extending parallel to the needle to move the needle into and out of the target vein.

According to a further illustrative embodiment of the present disclosure, a method of inserting a percutaneously placed device into a target vein includes the steps of providing an ultrasound probe, and providing a dispensing and control unit. The dispensing and control unit includes a percutaneously placed device, a first actuator configured to move the percutaneously placed device within a first degree of freedom, and a second actuator configured to move the percutaneously placed device within a second degree of freedom. A first position sensor is configured to detect the relative position of the first actuator, and a second position sensor configured to detect the relative position of the second actuator. The method further includes the steps of capturing an image from the ultrasound probe of a subcutaneous vein, and processing the image to decompose the image into the separate objects, including the border of the target vein. The method also includes the step of displaying, on a human machine interface, graphical representations of the border of the target vein, a longitudinal axis of the ultrasound probe, and a device mark. The method further includes the steps of manually moving the dispensing and control unit to align, on the human machine interface, the longitudinal axis of the ultrasound probe with the target vein, and activating the first actuator to move the percutaneously placed device within the first degree of freedom to align, on the human machine interface, the device mark with the target vein. The method also includes the steps of activating the second actuator to move the percutaneously placed device within the second degree of freedom to cause the percutaneously placed device to penetrate the target vein, and activating the second actuator to move the percutaneously placed device within the second degree of freedom to cause the needle to withdraw from the target vein.

While the nature and advantages of the present invention will be more fully appreciated from the following drawings and detailed description, showing the contemplated novel construction, combinations and elements as herein described, and more particularly defined by the appended claims, it is understood that changes in the precise embodiments of the present invention are meant to be included within the scope of the claims, except insofar as they may be precluded by the prior art.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments elected for description have been chosen to enable one skilled in the art to practice the invention. As used herein, when referring to the device of the present invention the term "proximal" will refer to the portion of the device closest to the operator and the term "distal" will refer to the portion of the device furthest from the operator.

Figure 1:
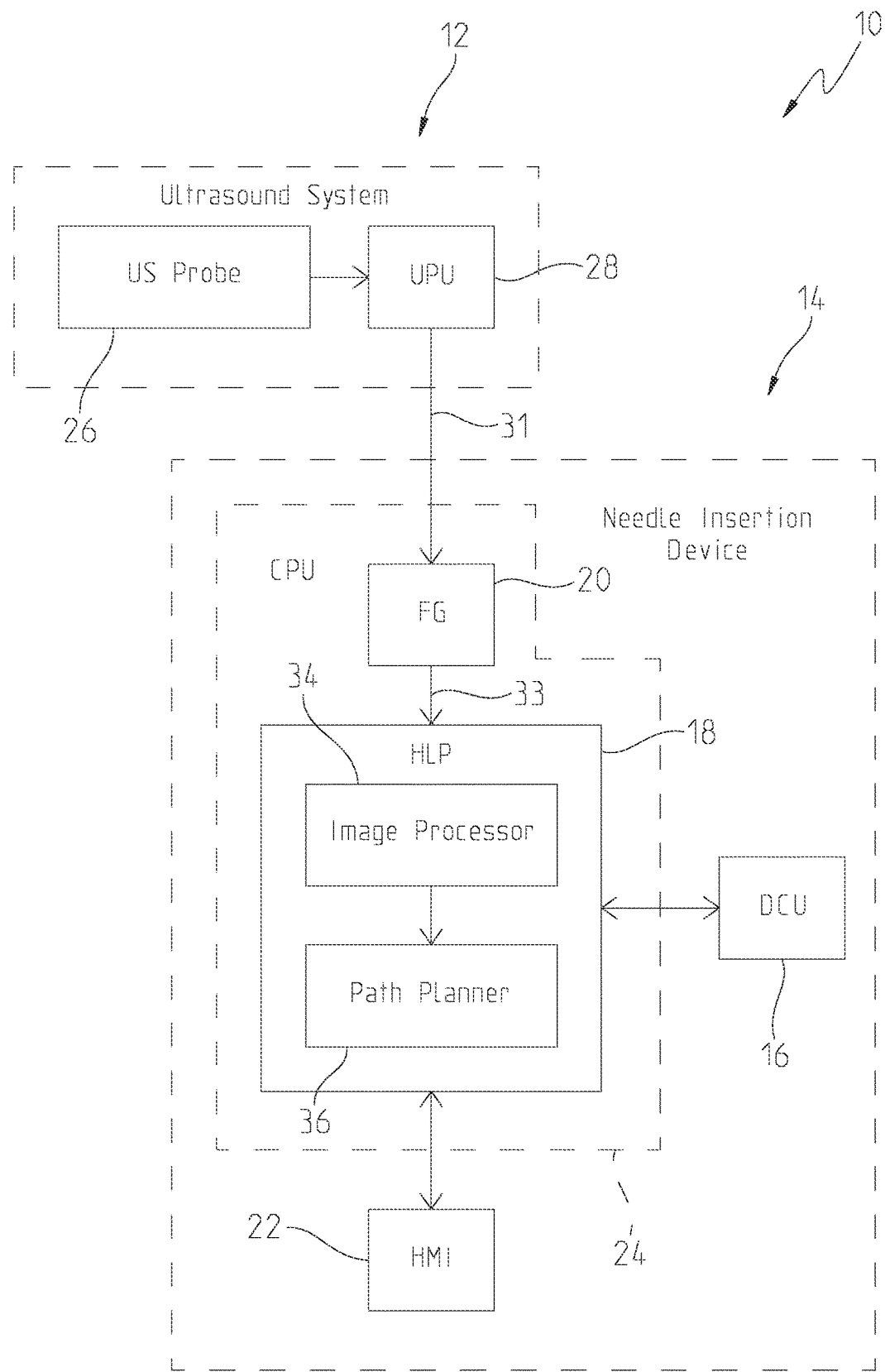
FIG. 1 is a block diagram of the image guided autonomous needle insertion system of the present disclosure.

With reference initially to FIG. 1, an illustrative image guided autonomous needle insertion system 10 is shown as including a conventional ultrasound system (US) 12 coupled to a percutaneous or needle insertion device 14. The needle insertion device 14 illustratively includes the following sub-systems: (1) a dispenser and control unit (DCU) or delivery system 16, (2) a high level processor (HLP) or main processor 18, (3) a frame grabber (FG) or frame processing system 20, and (4) a human machine interface (HMI) 22. The high level processor 18 and the frame grabber 20 may be incorporated within a central processing unit (CPU) 24 defined by a conventional laptop computer or part of an embedded system.

Figure 4:
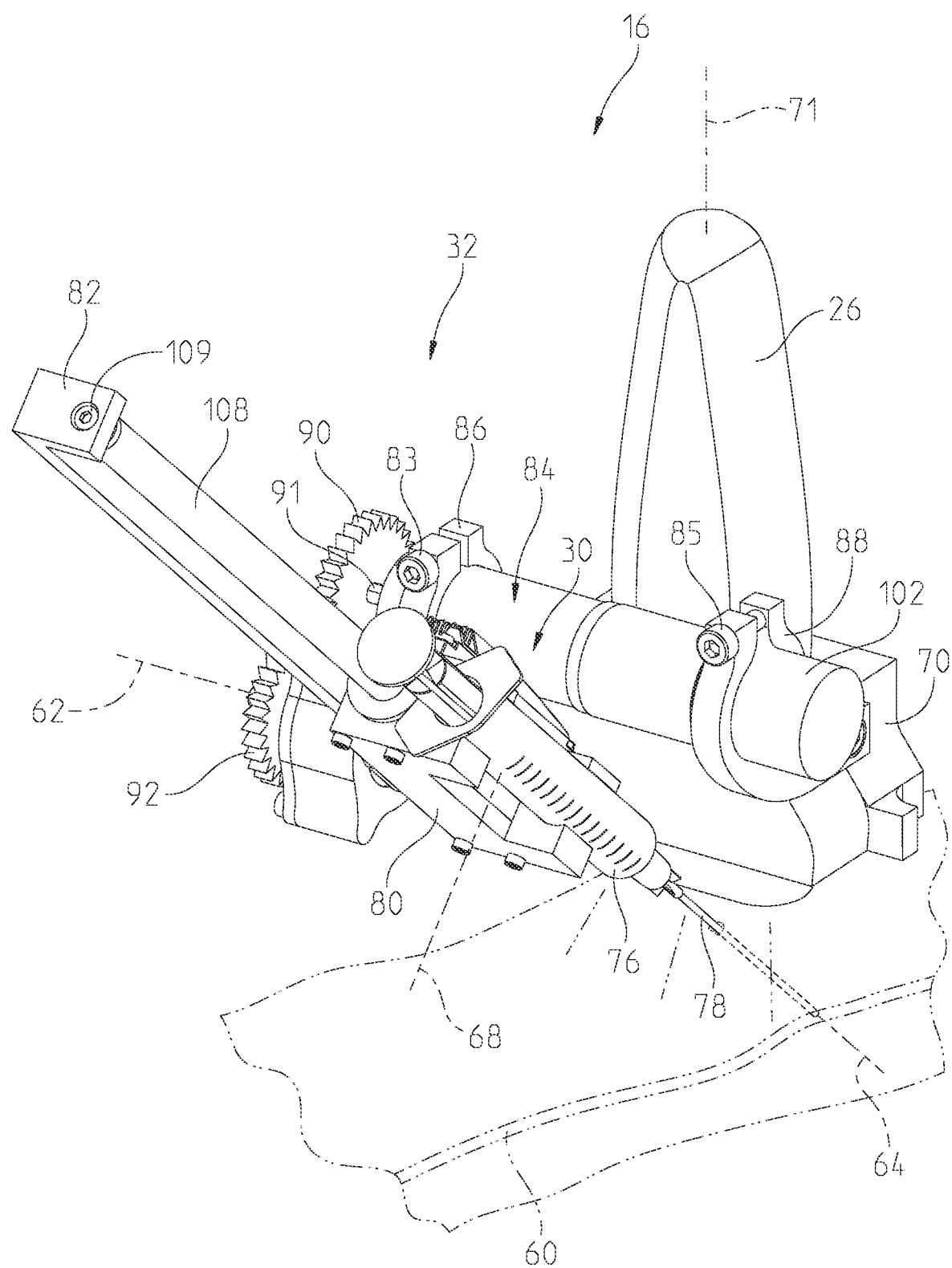
FIG. 4 is a front perspective view of the delivery system of FIG. 1, the delivery system shown in a front mounting configuration.

With reference to FIGS. 1 and 4, the ultrasound system 12 includes an ultrasound probe (UP) 26 coupled to an ultrasound processing unit (UPU) 28. The illustrative dispenser and control unit 16 includes a percutaneously placed device, such as a needle assembly 30, supported for movement by a drive mechanism 32. More particularly, the dispenser and control unit 16 controls three-dimensional (3D) position, rotation and penetration velocity of the needle assembly 30. As further detailed herein, the dispenser and control unit 16 provides multiple degrees of freedom to the needle assembly 30 (i.e., at least two degrees of freedom). While needle assembly 30 is further detailed herein as the illustrative percutaneously placed device, it should be appreciated that other devices may be used with the system 10 of the present disclosure. For example, a variety of biopsy devices, ablation devices (including radiofrequency ablation (RFA) devices), biopsy guns, cryoprobes and microwave probes could be used with the illustrative system 10.

The ultrasound processing unit 28 provides in real time to the frame grabber 20, data in either digital or analog formats representative of at least one of a display screen, a processed ultrasound image, and ultrasound raw data. Illustratively, ultrasound video 31 from the ultrasound system 12 is captured by the frame grabber 20. The frame grabber 20, in turn, provides an ultrasound image 33 to the high level processor 18. The high level processor 18 defines the optimal trajectory of the needle assembly 30, performs real time processing of the ultrasound image 33, and interfaces with the human machine interface 22, and the dispenser and control unit 16.

The high level processor 18 illustratively includes an image processor 34 and a path planner 36. The image processor 34 analyzes the information provided by the ultrasound system 12 (e.g., ultrasound images 33), detects regions of interest (ROI), and tracks movements of the needle assembly 30. The path planner 36 searches for an optimal trajectory of the needle assembly 30, follows execution (e.g., movement of the needle assembly 30), and provides real time adaptation if necessary. The human machine interface 22 provides input and output tools for the operator.

Figure 2:
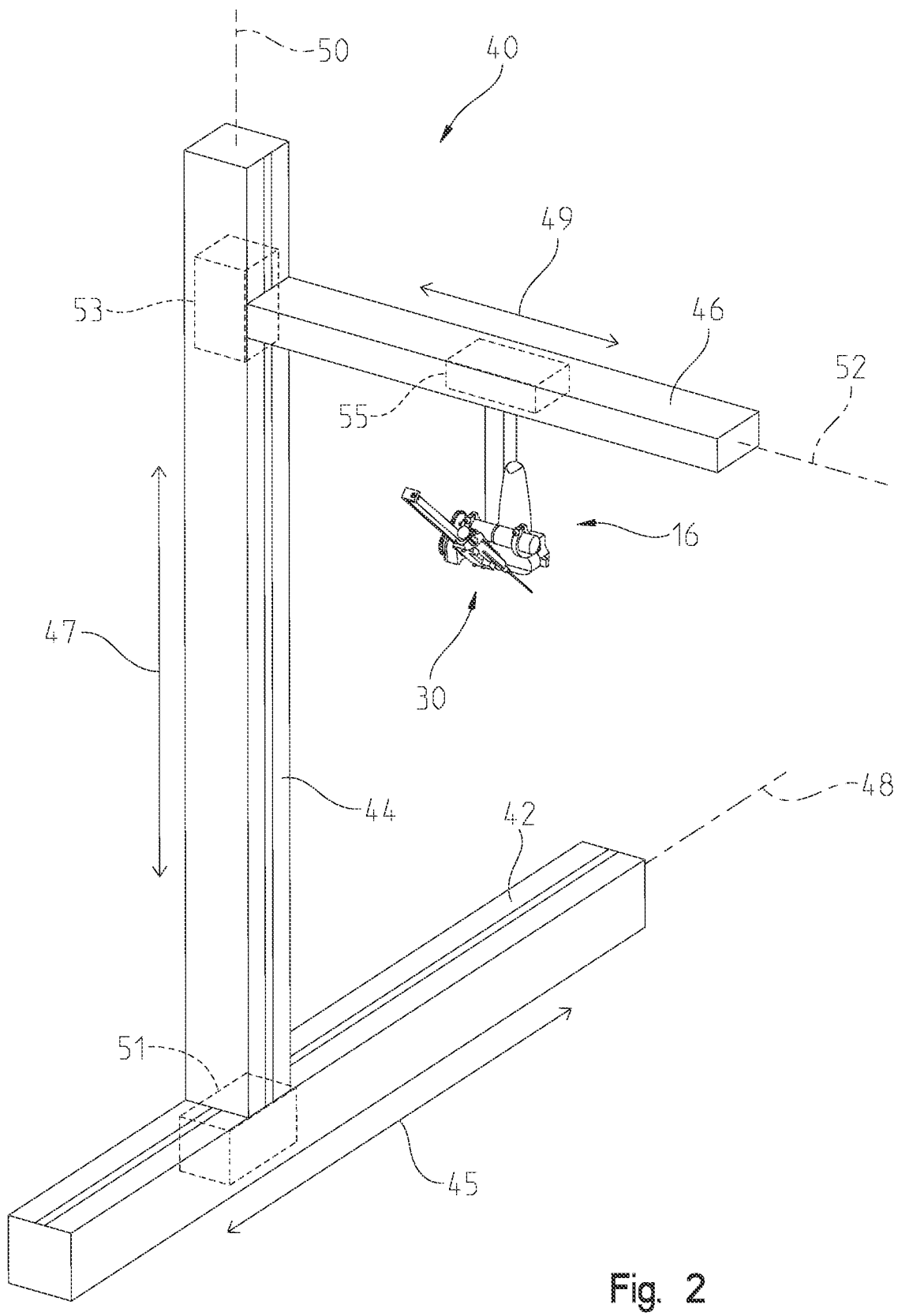
FIG. 2 is a perspective view of the delivery system of FIG. 1 supported by a stand including movable members.
Figure 3:
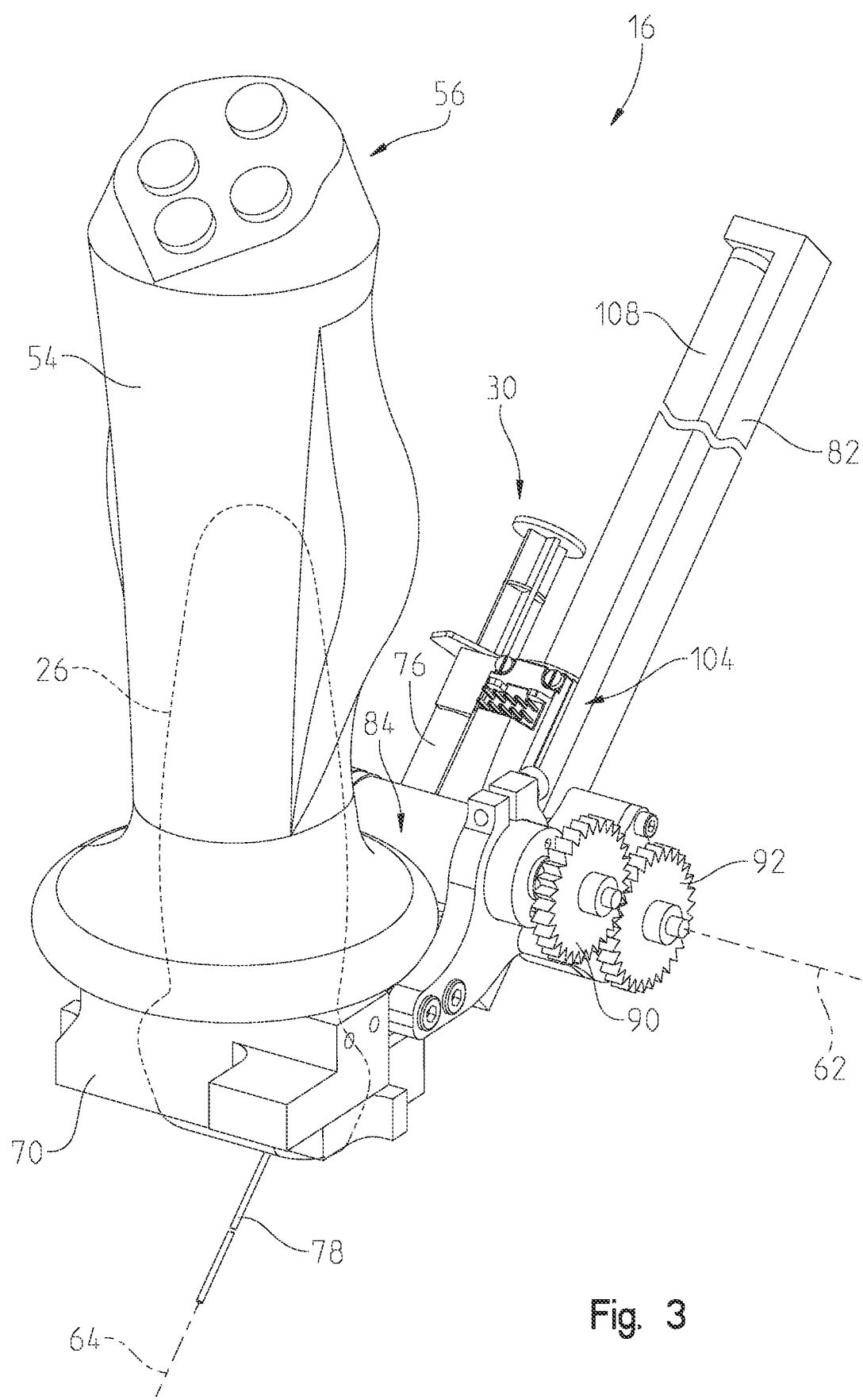
FIG. 3 is a perspective view of the delivery system of FIG. 1 configured to be manipulated by hand through a joystick control, the delivery system shown in a front mounting configuration.

The dispenser and control unit 16 is illustratively coupled to the ultrasound probe 26. The dispenser and control unit 16 may be supported by a stand 40 (FIG. 2), or may be hand-held (FIG. 3). In the illustrative embodiment of FIG. 2, the stand 40 includes a base 42, an upright 44, and a cantilevered arm 46. The upright 44 is supported for movement (as represented by arrows 45) relative to the base 42 along a first axis 48, the cantilevered arm 46 is supported for movement (as represented by arrows 47) relative to the upright 44 along a second axis 50, and the dispenser and control unit 16 is supported for movement (as represented by arrows 49) relative to the cantilevered arm 46 along a third axis 52. First, second and third actuators 51, 53 and 55 (such as electric motors) are illustratively configured to move the upright 44, the cantilevered arm 46, and the dispenser and control unit 16, respectively. Such actuators 51, 53 and 55 may be coupled to the central processing unit 24 for operation by the operator through input to the human machine interface 22.

As further detailed herein, the dispenser and control unit 16 shown in FIG. 3 is configured to be hand-held by an operator. Illustratively, a handle 54 is defined by a joystick 56 which is supported by the ultrasound probe 26. More particularly, the joystick 56 may have an upwardly extending chamber configured to receive the ultrasound probe 26. As such, the dispenser and control unit 16, including the needle assembly 30, may be manually manipulated by the operator. The handle 54 may be secured to the ultrasound probe 26 in any conventional manner, such as through a friction fit or fasteners.

While the handle 54 may be formed similar to the joystick 56 shown in FIG. 3, it should be appreciated that the handle 54 may take other configurations. In yet other illustrative embodiments, the ultrasound probe 26 may be supported separately from (i.e., in spaced relation to) the dispenser and control unit 16. For example, the ultrasound probe 26 may include a hand grip for independent manipulation by a user separate from the dispenser and control unit 16. As such, the dispenser and control unit 16 can be either applied to any commercial ultrasound device, or the ultrasound device can be integrated with the system 10.

Figure 5:
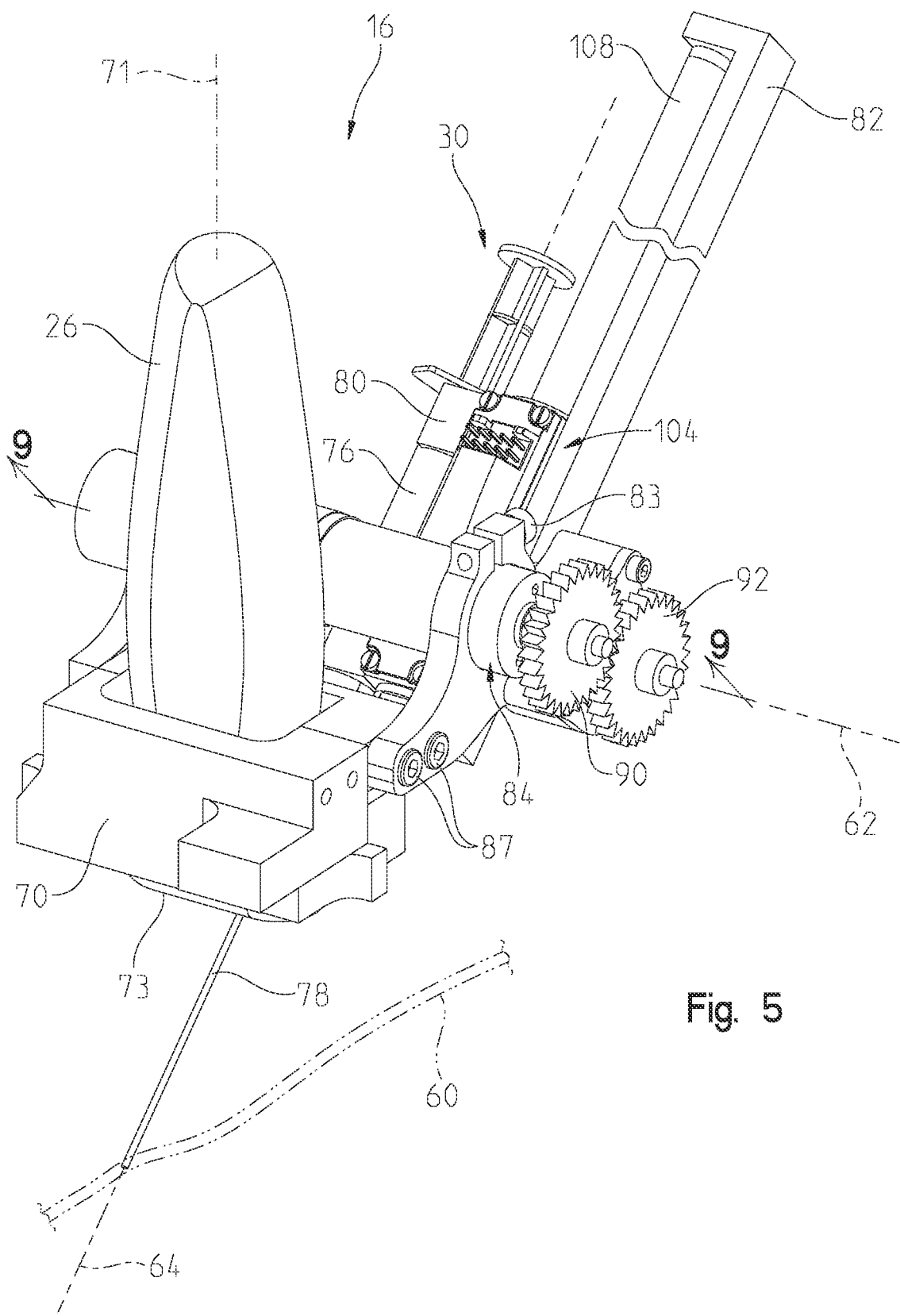
FIG. 5 is a rear perspective view of the delivery system of FIG. 4.
Figure 6:
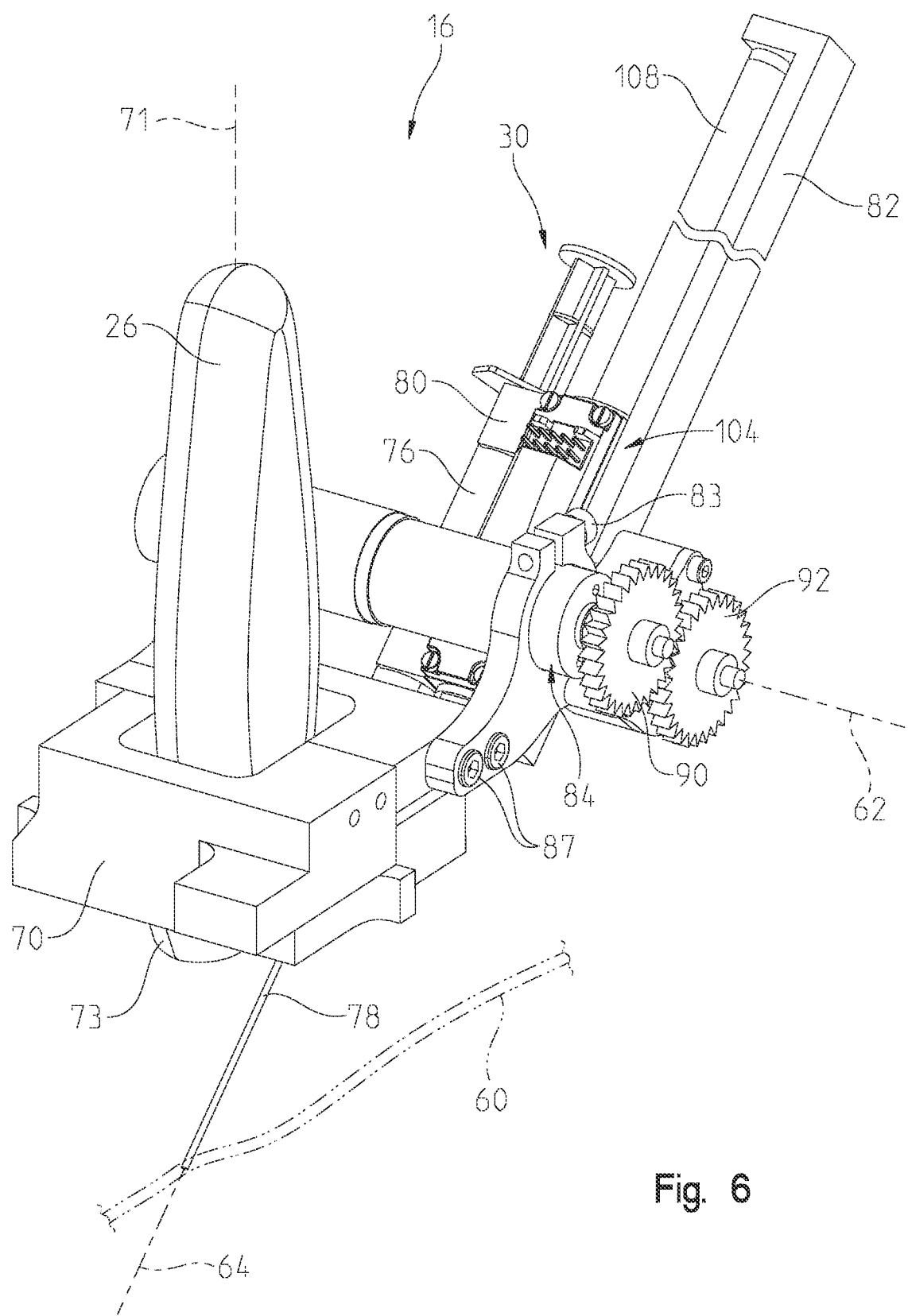
FIG. 6 is a rear perspective view of an alternative delivery system shown in a side mounting configuration.
Figure 7:
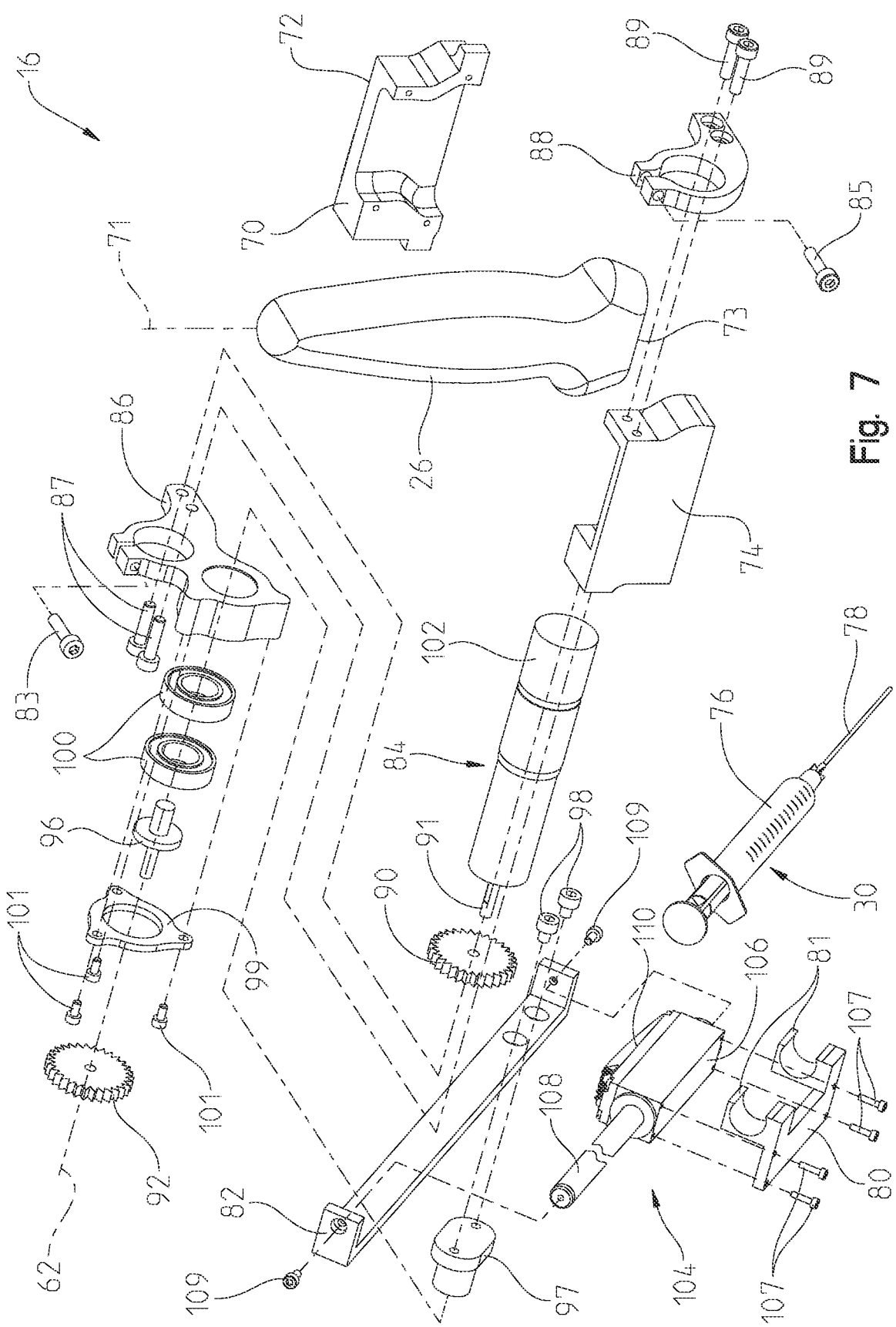
FIG. 7 is a front exploded perspective view of the delivery system of FIG. 4.
Figure 8:
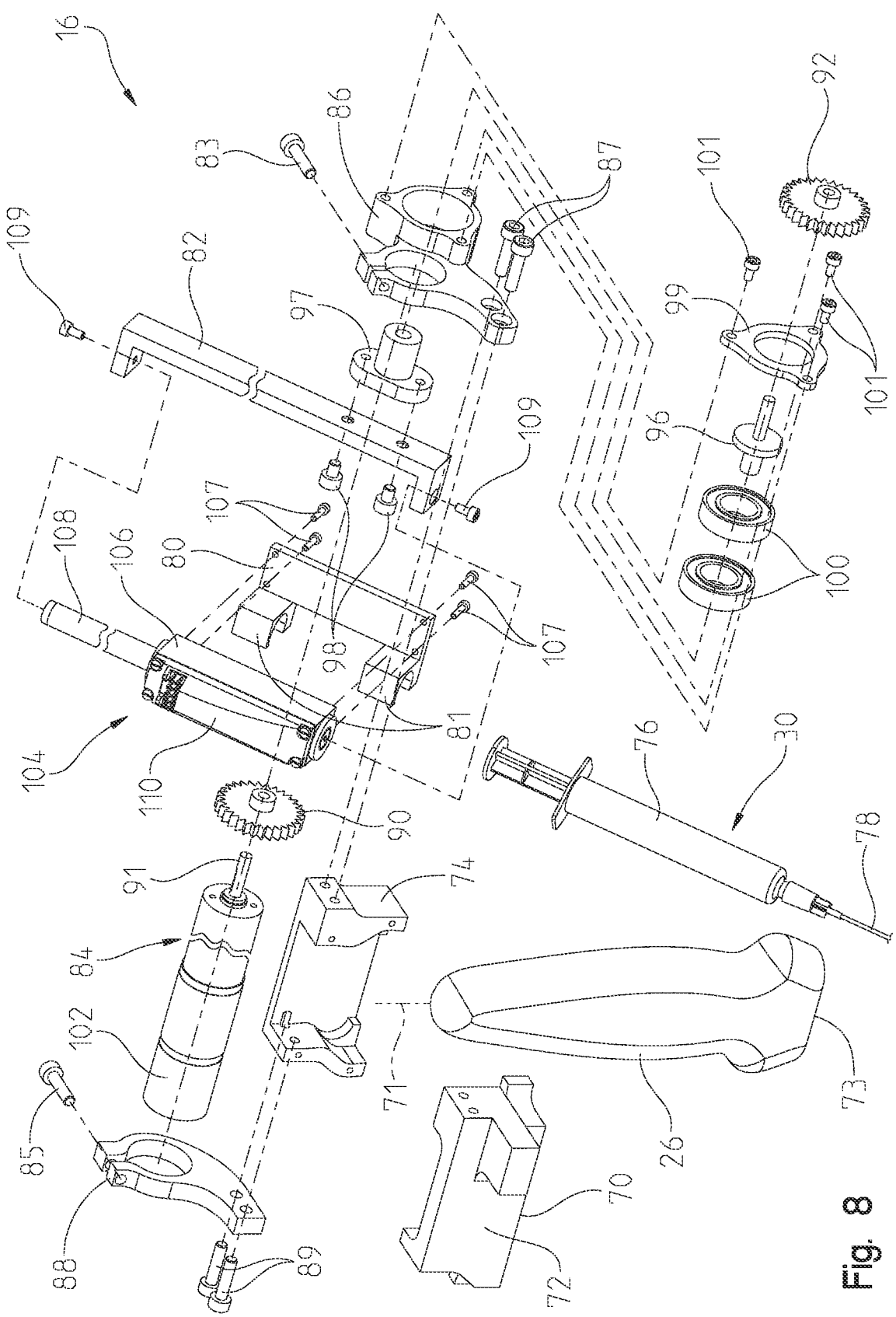
FIG. 8 is a rear exploded perspective view of the delivery system of FIG. 4.
Figure 9:
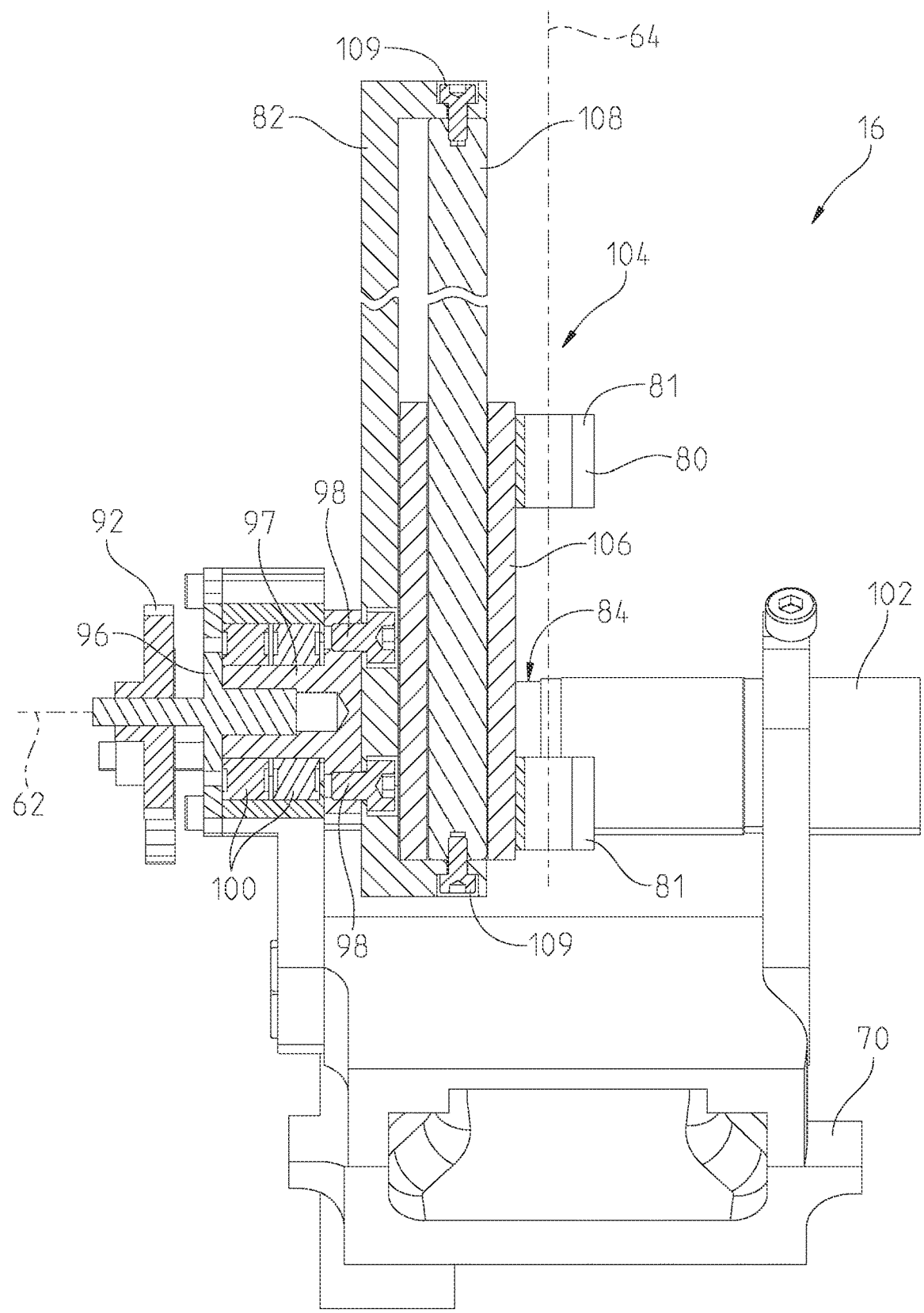
FIG. 9 is a cross-sectional view taken along line 9-9 of FIG. 5.

The ultrasound probe 26 may be coupled to the dispenser and control unit 16 in a front mounting arrangement or configuration (FIGS. 4 and 5), or in a side mounting arrangement or configuration (FIG. 6). With reference to FIGS. 4 and 5, the front mounting configuration is defined when the ultrasound probe 26 is mounted in the wide direction relative to a subcutaneous target vein 60 (i.e., when its major transverse axis extends perpendicular to the target vein 60).

With reference to FIG. 6, the side mounting configuration is defined when the ultrasound probe 26 is mounted in the short direction relative to the subcutaneous target vein 60 (i.e., when its major transverse axis extends parallel to the target vein 60). As shown, the front mounting configuration of the ultrasound probe 26 is oriented ninety degrees about longitudinal axis 71 relative to the side mounting configuration.

The ultrasound probe 26 may comprise any conventional two or three dimensional ultrasound probe. In one illustrative embodiment, the ultrasound probe 26 comprises Model L25 ultrasound transducer available from SonoSite, Inc. of Bothell, Wash., USA.

With reference to FIG. 4, the dispenser and control unit 16 may be configured to provide multiple degrees of freedom to the needle assembly 30. Illustratively, the needle assembly 30 may have between two to five degrees of freedom. In the illustrative embodiment dispenser and control unit 16 of FIG. 4 configured for insertion into subcutaneous target vein 60, the needle assembly 30 is provided with two degrees of freedom (rotation about an x-axis 62 for needle alignment with the vein 60, and translation along a z-axis 64 for needle penetration into and withdrawal from the vein 60). The x-axis 62 is defined as extending perpendicular to a longitudinal axis 66 of the needle assembly 30, while the z-axis 64 is defined as extending parallel to the longitudinal axis 66 of the needle assembly 30. Other degrees of freedom may include rotation about a y-axis 68, translation along the x-axis 62, and translation along the y-axis 68.

With reference to FIGS. 4-9, the dispenser and control unit 16 illustratively includes a sensor holder or mount 70 coupled to the ultrasound probe 26. As detailed above, in certain illustrative embodiments, the ultrasound probe 26 is not secured to the dispenser and control unit 16 such that the ultrasound probe 26 may be manipulated independently. The ultrasound probe 26 defines a longitudinal center axis 71, and is oriented such that its operating head 73 is downwardly facing. The sensor holder 70 includes first and second u-shaped members or clamps 72 and 74 secured to opposite sides of the ultrasound probe 26. The needle assembly 30 illustratively includes a syringe 76 and a needle 78. A syringe holder 80 illustratively couples the needle assembly 30 to a z-bar holder 82. More particularly, the syringe holder 80 includes C-shaped receiving arms 81 to receive the syringe 76.

A first actuator 84, illustratively an electrical motor, is operably coupled to the sensor holder 70 through first and second motor holders or mounts 86 and 88. More particularly, bolts 83 and 85 clamp the first and second motor holders 86 and 88 to opposing ends of the motor 84. Bolts 87 and 89 couple the first and second motor holders 86 and 88 to the member 74 of mount 70. The first actuator 84 is in electrical communication with the high level processor 18.

A drive gear 90 is operably coupled to a rotatable drive shaft 91 of the first actuator 84, while a driven gear 92 is operably coupled to a lower end of the z-bar holder 82. More particularly, the driven gear 92 is rotatable coupled to the z-bar holder 82 through a gear pin 96 which, in turn, is coupled to a z-bar shaft 97. Bolts 98 secure the z-bar shaft 97 to the z-bar holder 82. Bearings 100 are supported between the motor holder 86 and the z-bar shaft 97 and receive the z-bar shaft 97 for rotation therein. A gear cover 99 is secured in position through bolts 101. The first actuator 84 is configured to rotate the z-bar holder 82 about the x-axis 62. A position sensor 102, such as an encoder, is illustratively operably coupled to the motor 84 to detect the rotational position of the z-bar holder 82 (and thereby the syringe holder 80 and the needle assembly 30) about the x-axis 62, and may provide a signal indicative thereof to the high level processor 18.

The z-bar holder 82 supports a second actuator, illustratively an electrical linear motor 104. The second actuator 104 is illustratively in electrical communication with the high level processor 18. The linear motor 104 illustratively includes a housing 106 coupled to the syringe holder 80, and a rod 108 coupled to the z-bar holder 82. Illustratively, the housing 106 of the linear motor 104 is coupled to the syringe holder 80 through bolts 107, while opposing ends of the rod 108 are secured to the z-bar holder 82 through bolts 109. The linear motor 104 is configured to move in translation the syringe holder 80 and the needle assembly 30 relative to the z-bar holder 82 along the z-axis 64. More particularly, the housing 106 is configured to move, along with the syringe holder 80, linearly along the rod 108.

In one illustrative embodiment, the linear motor 104 may comprise a linear DC servomotor series LM 1247 available from Faulhaber of Schonaich, Germany. A position sensor 110, such as an encoder, may be coupled to the linear motor 104 to determine the position of the syringe holder 80 (and thereby the needle assembly 30) relative to the z-bar holder 82, and provide a signal indicative thereof to the high level processor 18. More particularly, the encoder 110 is configured to determine the relative position of the housing 106 along the rod 108. The penetration speed of the needle 78 as determined by the motor 104 is illustratively between 0 to 250 cm/sec.

Figure 10:
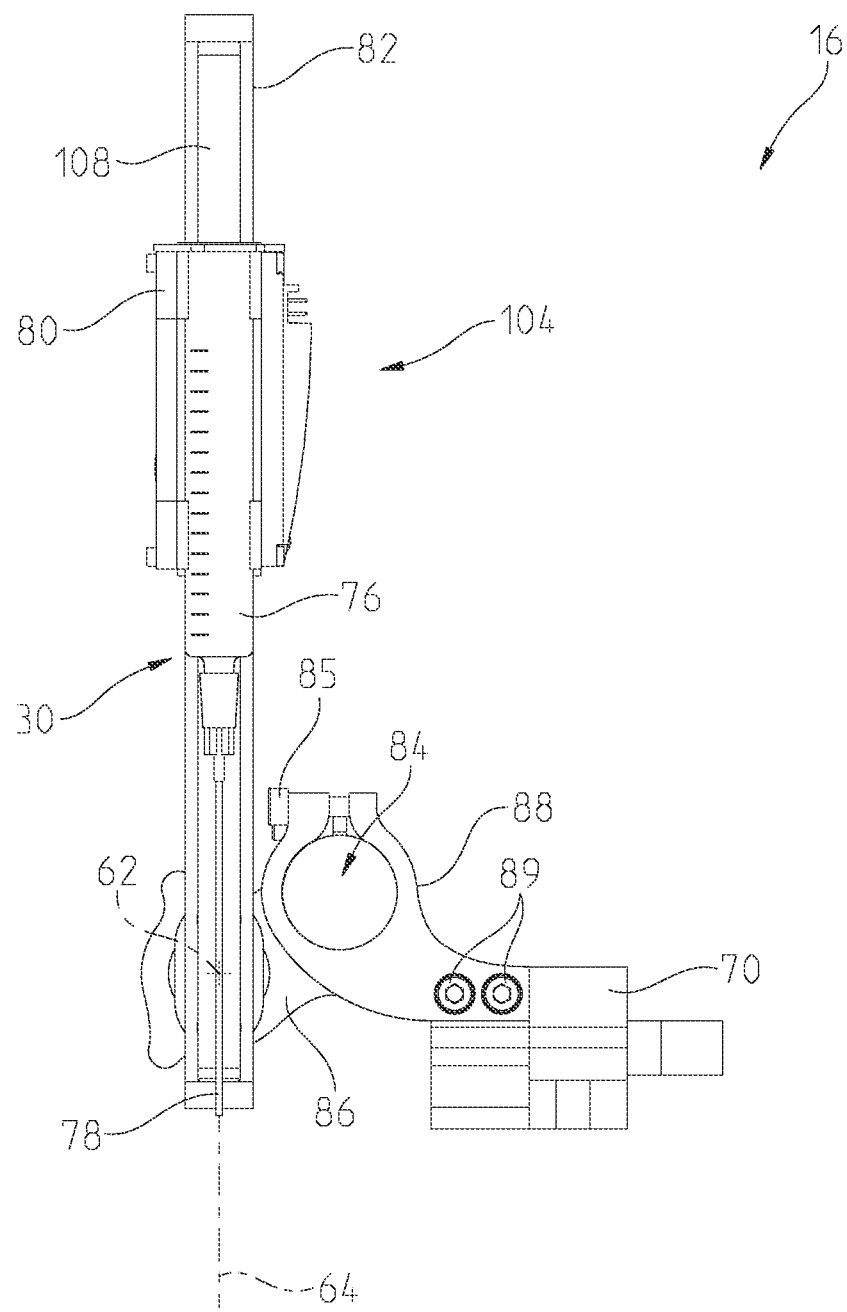
FIG. 10 is a side elevational view of the delivery system of FIG. 4, with the needle shown in a first, withdrawn position.
Figure 11:
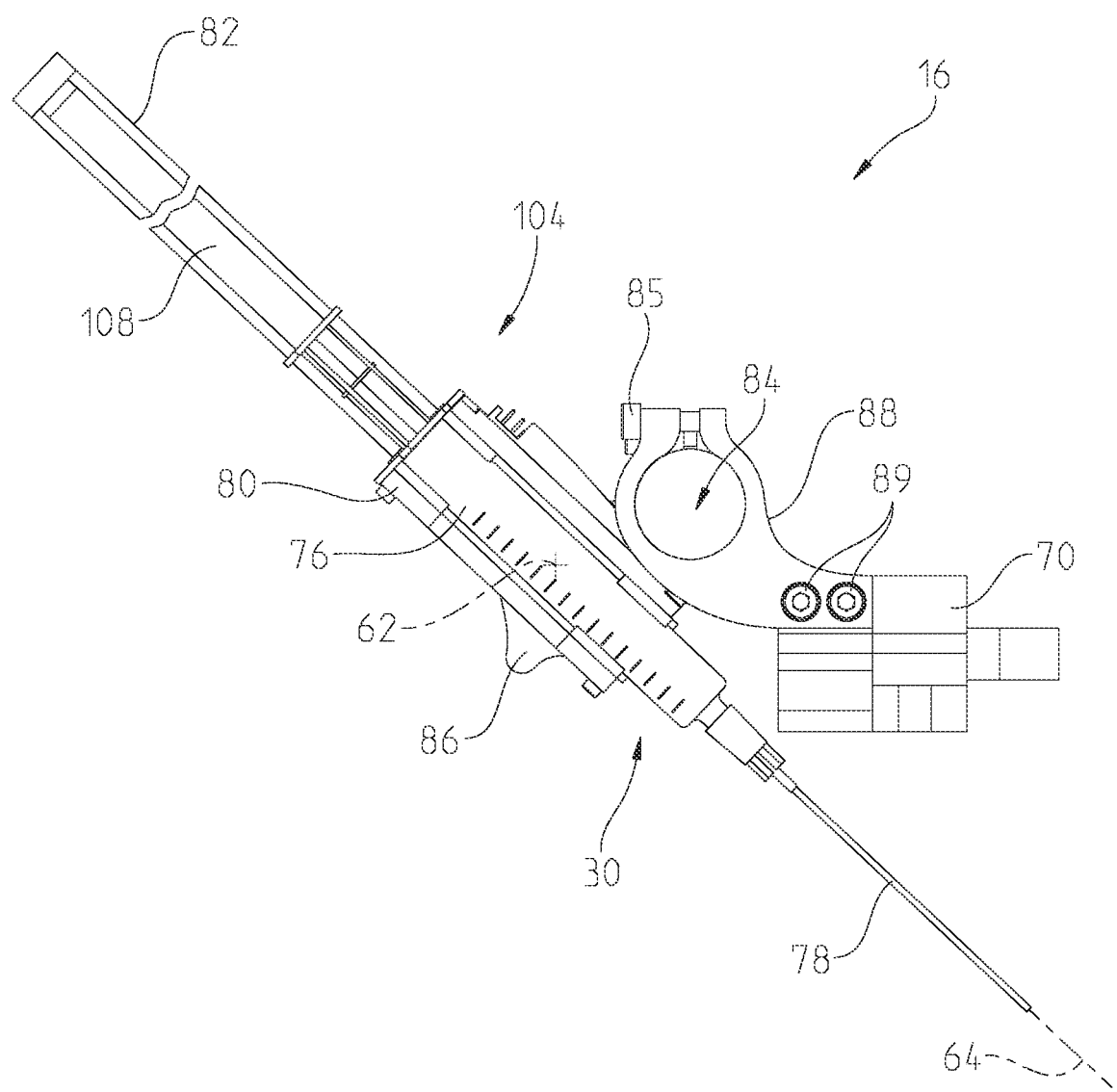
FIG. 11 is a side elevational view of the delivery system of FIG. 4, with the needle shown in a second, inserted position.

FIG. 10 illustrates the first and second actuators 84 and 104 positioning the needle 78 in a first, withdrawn position. FIG. 11 illustrates the first and second actuators 84 and 104 positioning the needle 78 in a second, inserted position. More particularly, the first actuator 84 illustratively rotates the needle assembly 30 about the x-axis 62 in a counter-clockwise direction from FIG. 10 to FIG. 11, while the second actuator 104 illustratively translates the needle assembly 30 along the z-axis 64 from a raised position to a lowered position from FIG. 10 to FIG. 11.

As further detailed herein, joystick 56 may be supported by the ultrasound probe 26 (FIGS. 12 and 13) to define a user interface. Alternative configurations of the handle 54 may be supported by the ultrasound probe 26, together with, or independent of, the dispenser and control unit 16. More particularly, different covers may be supported by the probe 26 to define different contoured gripping surfaces. In other illustrative embodiments, the handle 54 may be supported independently and separately from the probe 26.

With reference to FIGS. 14-18, a further illustrative dispenser and control unit 16' is configured to provide three degrees of freedom to the needle assembly 30 (rotation about an x-axis 62 for needle alignment with a vein 60, translation along the x-axis 62 for needle alignment with the vein, and translation along z-axis 64 for needle penetration into and withdrawal from the vein 60). The dispenser and control unit 16' illustratively includes many similar components to the dispenser and control unit 16 further detailed above. As such, similar components will be identified with like reference numbers.

The dispenser and control unit 16' illustratively includes a sensor holder 70' coupled to the ultrasound probe 26. The sensor holder 70' includes first and second u-shaped members or clamps 72' and 74' secured to opposite sides of the ultrasonic probe 26. A syringe holder 80' illustratively couples the needle assembly 30 to z-bar holder 82. First actuator 84 is operably coupled to sensor holder 70' through first and second motor holders or mounts 86' and 88', illustratively defined by a movable support or carriage 164. Opposing ends of a rod 166 extend between supports 167 of the member 74', wherein the rod 166 supports the carriage 164. More particularly, a boss 168 of the carriage 164 slidably receives the rod 166.

Drive gear 90 is operably coupled to rotatable drive shaft 91 of the first actuator 84, while driven gear 92 is operably coupled to a lower end of z-bar holder 82. More particularly, the driven gear 92 is rotatably coupled to the z-bar holder 82 through a gear pin 96'. Bearing 100 is supported by the motor holder 86' and receives the gear pin 96' for rotation therein. The first actuator 84 is configured to rotate the z-bar holder 82 about the x-axis 62.

The z-bar holder 82 supports a second actuator, illustratively an electrical linear motor 104. The linear motor 104 is illustratively configured to move in translation the syringe holder 80' and the needle assembly 30 relative to the z-bar holder 82 along the z-axis 64. More particularly, the housing 106 is configured to move, along with the syringe holder 80, along the rod 108.

A third actuator, illustratively an electrical linear motor 170, is configured to move in translation the syringe holder 80 along the x-axis 62. The third actuator 170 is illustratively in electrical communication with the high level processor 18. The linear motor 170 illustratively includes a housing 172 coupled to the carriage 164, and a rod 174 coupled to the member 74'. More particularly, opposing ends of the rod 174 extend between supports 175 of the member 74'. A position sensor 176, such as an encoder, may be coupled to the linear motor 170 to determine the position of the syringe holder 80' (and thereby the needle assembly 30) relative to the z-bar holder 82 along the x-axis 62, and provide a signal indicative thereof to the high level processor 18. More particularly, the encoder 176 is configured to determine the relative position of the housing 172 along the rod 174.

The path or trajectory of the needle 78 is estimated by the path planner 36 which sends the required path coordinates and speed. The penetration plan is then transferred to the dispenser and control unit 16 for controlling operation of the motors 84 and 104. The penetration force of the needle 78 is estimated by measuring the electric current required by the motor 104.

The dispenser and control unit 16 expected position error is illustratively between 1-2 mm depending on the image sensor resolution. A standard Ethernet or USB link, wired or wireless, may be used to communicate with external devices. The system 10 may be used as completely automated, semi-automated, operator supervised, and operator controlled. Following is a brief definition of illustrative system specifications:

| Parameter | Range | Distance from target | Unit |
|---|---|---|---|
| X | ±10.0 | ±2.0 | mm |
| Y | ±10.0 | ±2.0 | mm |
| Z | 0.0-100.0 | ±1.0 | mm |
| Insertion speed | 0.0-5.00 | ±0.01 | cm/s |
| Rotation angle | 180 | | degree |
| Penetration angle | 0-90 | ±0.5 | degree |

Interface options: USB or Ethernet
Power supply voltage: +3.2 to +16 volts DC
Power consumption: 160 mA (typical) @ 5 volts with . . .
Connector: TBD
Weight: 0.5-1.5 Kg
Dimensions: 130 mm×165 mm×75 mm
Needle types: Bevel, Trocar, Franseen, Conic, Blunt
Needle sizes: 7 to 26 Gauge The high level processor 18 illustratively defines the central control and processing unit. As such, the high level processor 18 is responsible of sending commands to the different units (e.g., the dispenser and control unit 16 and the human machine interface 22), processing information received from the ultrasound system 12, and processing information received from the operator through the human machine interface 22.

As further detailed herein, the image processor 34 analyzes the information provided by external sensors such as the ultrasound system 12, detects region of interest (ROI), and tracks needle 78 movements. The path planner 36 searches for an optimal solution (e.g., needle path), follows execution, and provides real time adaptation if necessary. The high level processor 18 interfaces between the dispenser and control unit 16 and the human machine interface 22. The path planner module estimates the optimum trajectory based on the geometry (FIG. 30) defined by the dispenser and control unit 16 and the needle 78 employed.

The path planner 36 computes high-level actions that will have the highest probability of avoiding obstacles while guiding the needle 78 to the target vein 60. For a given needle-tissue combination and a set of anatomical structures, there may be multiple feasible paths that the needle 78 could take to reach a target vein 60 while avoiding obstacles. The shortest path to the target vein 60 will ensure that most of the needle 78 is located inside the tissue.

As noted above, the high level processor 18 may be implemented in a standard laptop or desktop computer. In another implementation the high level processor 18 may be in an embedded system where the ultrasound image and human machine interface 22 controls are displayed and/or accessed.

Figure 23:
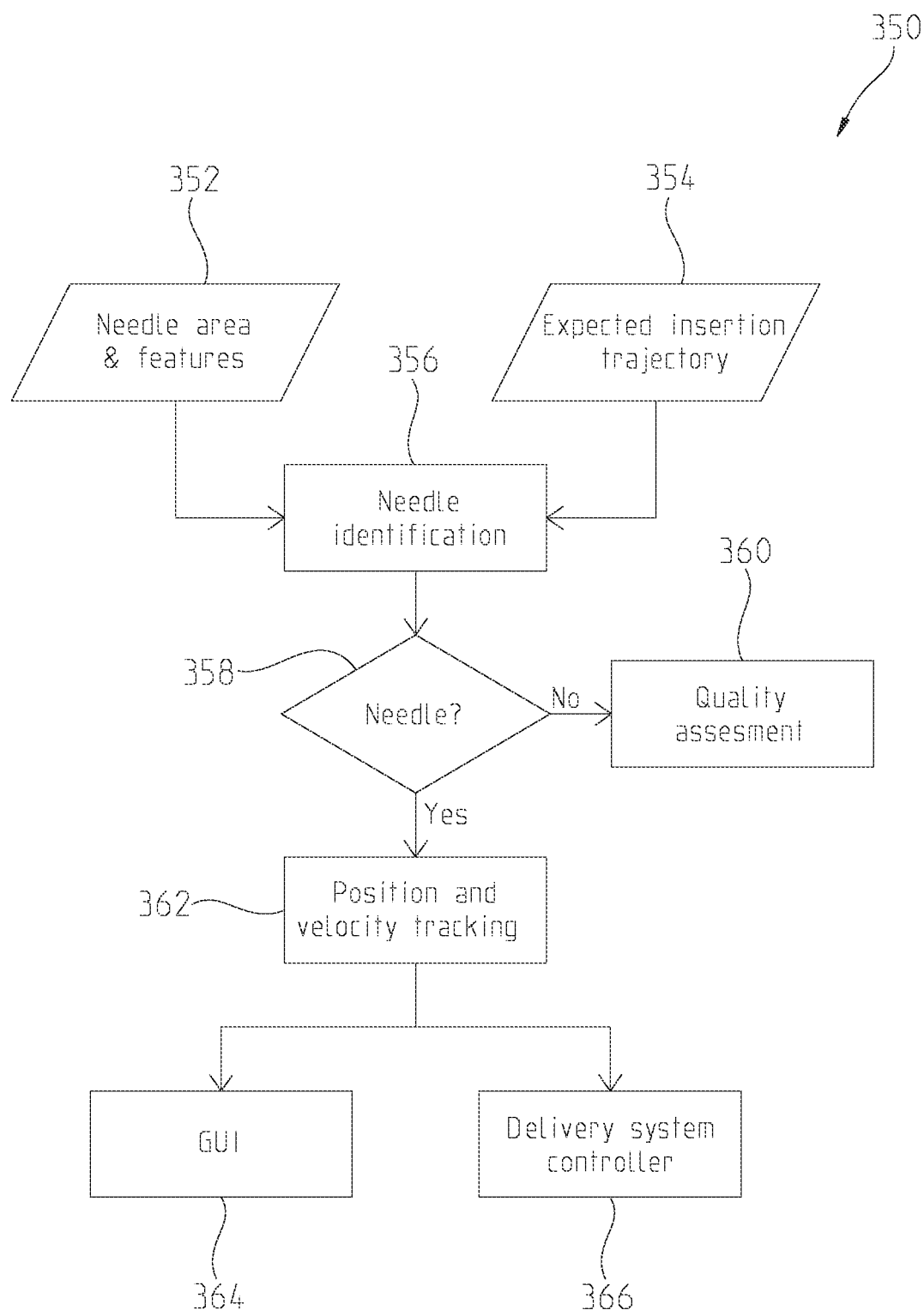
FIG. 23 is a flowchart of an illustrative needle detection and tracking module.
Figure 24:
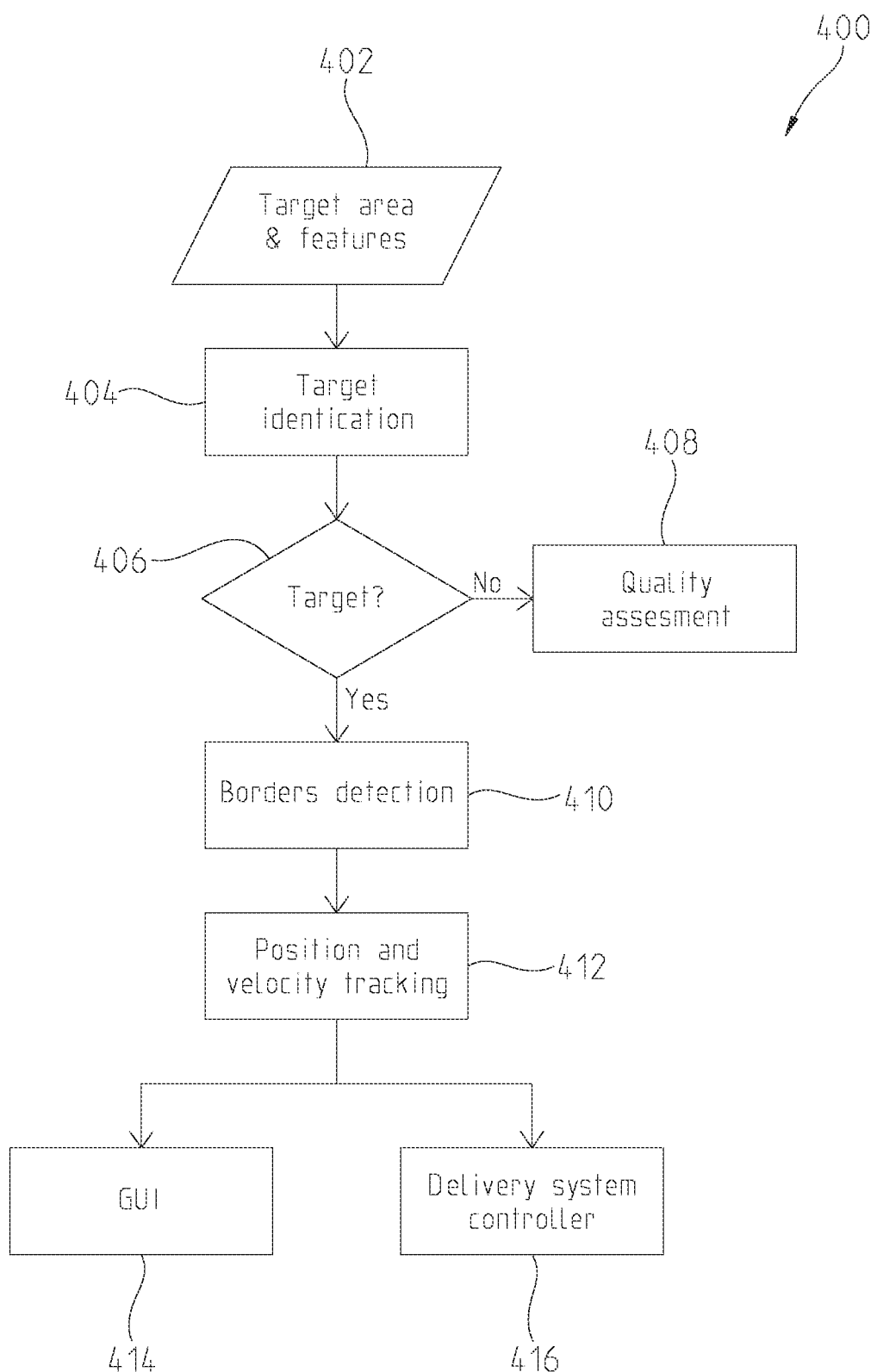
FIG. 24 is a flowchart of an illustrative target detection and tracking module.
Figure 25:
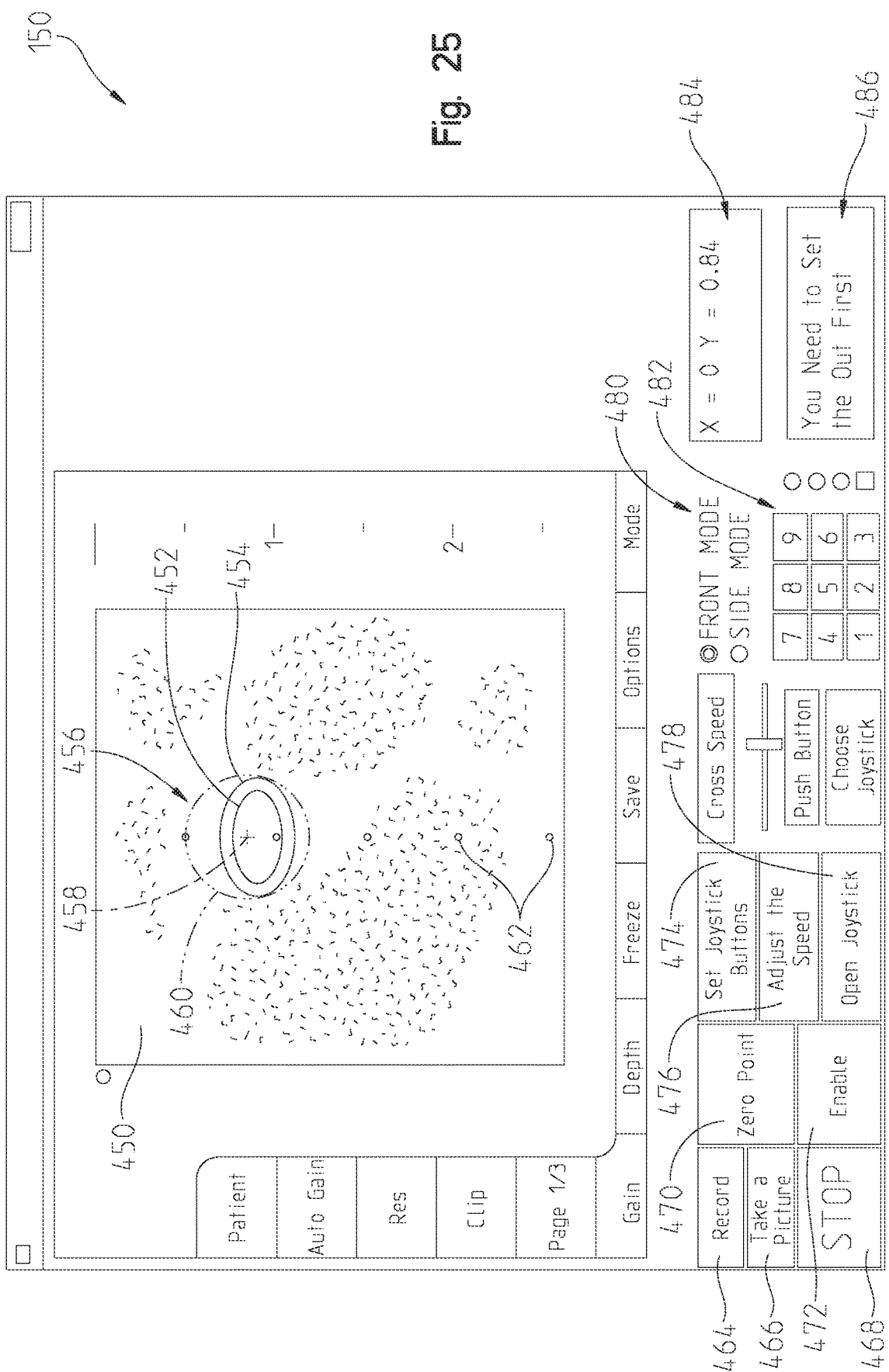
FIG. 25 is an illustrative view of the graphical user interface of the human machine interface, showing an original ultrasound image generated by the delivery system in the front mounting configuration of FIG. 4.

The high level processor 18 is responsible for processing the information coming from the ultrasound system 12, analyzing the operator commands from the human machine interface 22, enhancing and processing the ultrasound image 33 from the ultrasound system 12, estimating the optimal needle trajectory, sending commands to the dispenser and control unit 16, and monitoring the safety of the system 10. The high level processor 18 executes various software subroutines or modules, including an image processing module 200 (FIG. 19), an image preprocessing module 250 (FIG. 20), a background and object segmentation module 300 (FIG. 22), a device or needle detection and tracking module 350 (FIG. 23), and a target detection and tracking module 400 (FIG. 24).

Figure 27:
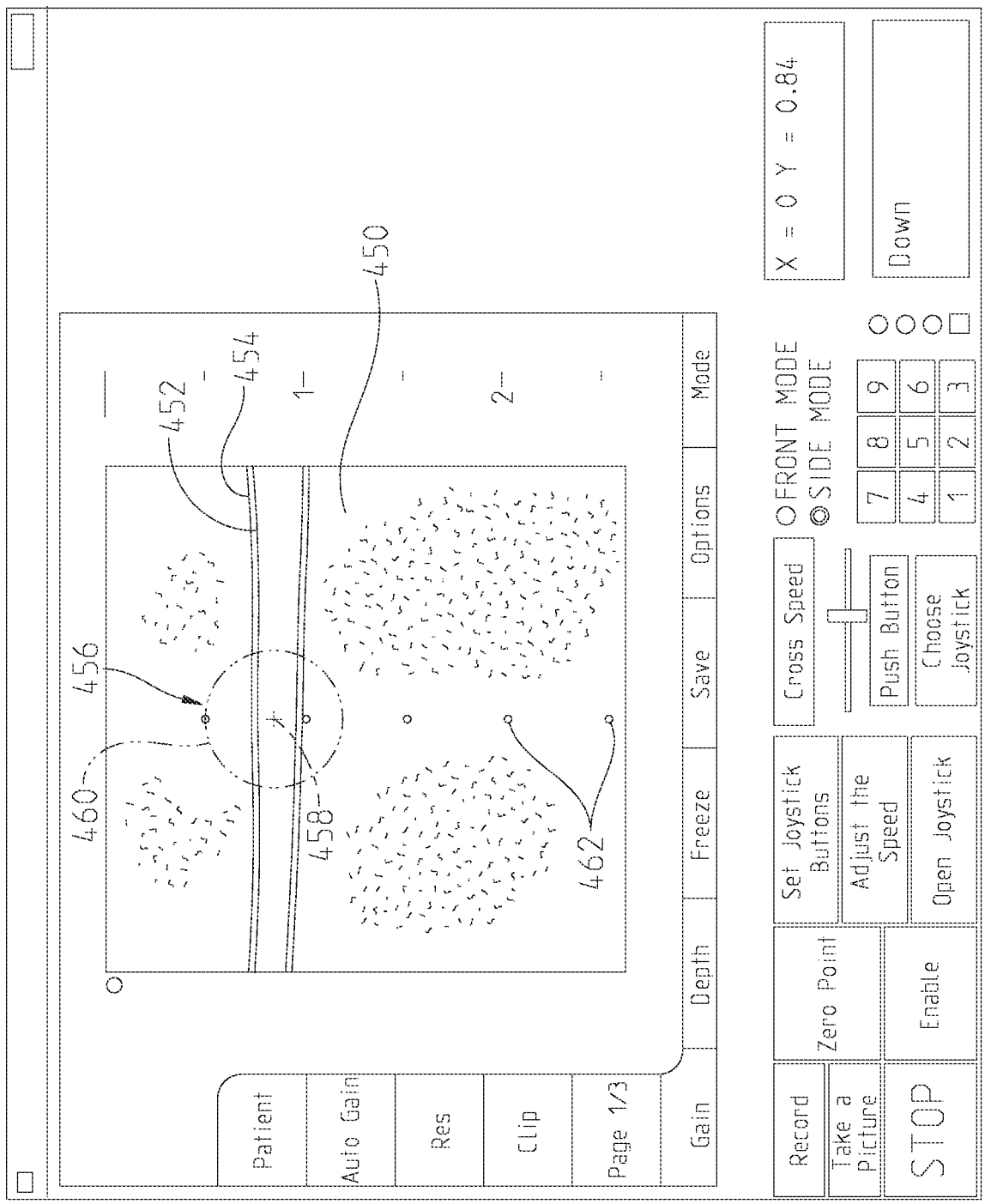
FIG. 27 is an illustrative view of the graphical user interface of the human machine interface, showing an original ultrasound image generated by the delivery system in the side mounting configuration of FIG. 6.

Once the system 10 is activated and calibrated, the operator searches for the target vein 60 and marks the point of penetration in the screen display or window area 450 by setting a mark (illustratively a cross-circle target) on the desired target vein 60 (FIG. 27). The position is found by either the operator setting the target manually with the joystick 56 or by confirming the vein or organ detection provided by the image processor 34. Once the position is confirmed by the operator, the coordinates of the target vein 60 relative to the ultrasound probe 26 are extracted from the ultrasound image 33.

The human machine interface 22 illustratively provides a graphical user interface (GUI) 150 including input tools for the operator. More particularly, the human machine interface 22 illustratively includes graphical user interface (GUI) 150 where the ultrasound information is displayed and command inputs are provided. FIGS. 25-34 illustrate a possible arrangement/design of the graphical user interface (GUI) 150.

Figure 13:
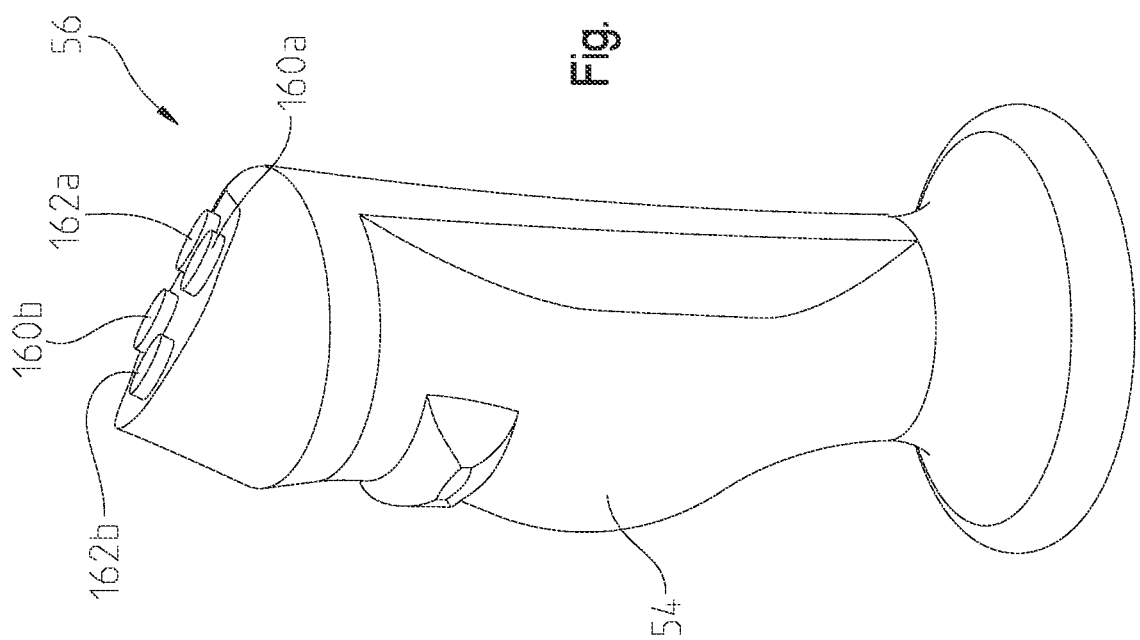
FIG. 13 is a rear perspective view of the joystick of the human machine interface of FIG. 12.
Figure 12:
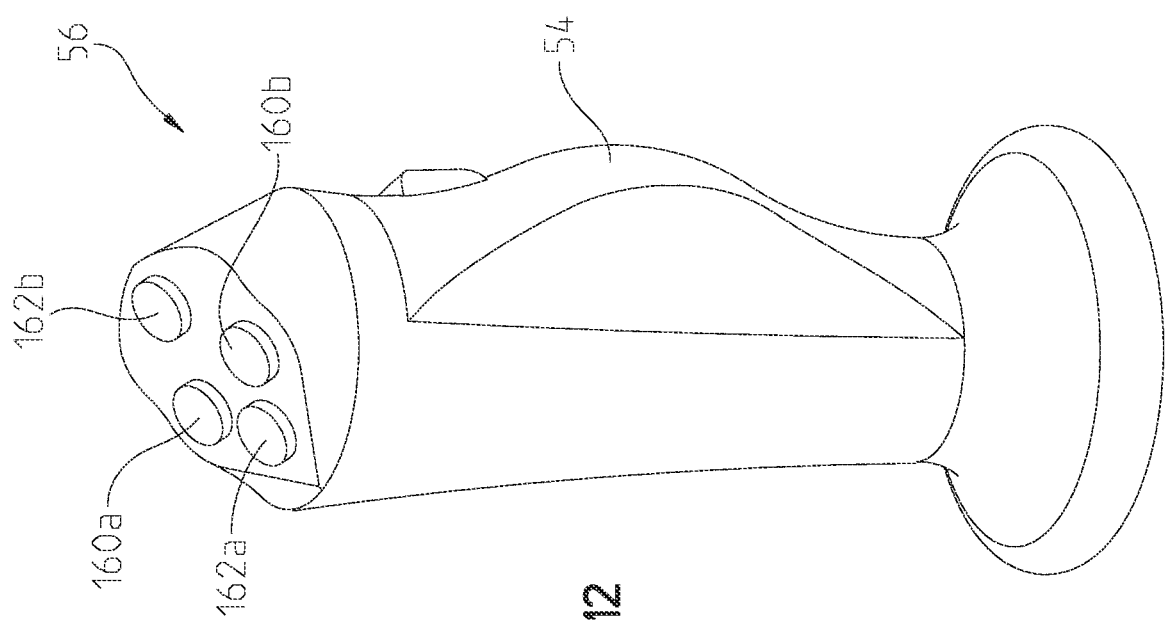
FIG. 12 is a front perspective view of a joystick of the human machine interface of the device of FIG. 1.
Figure 14:
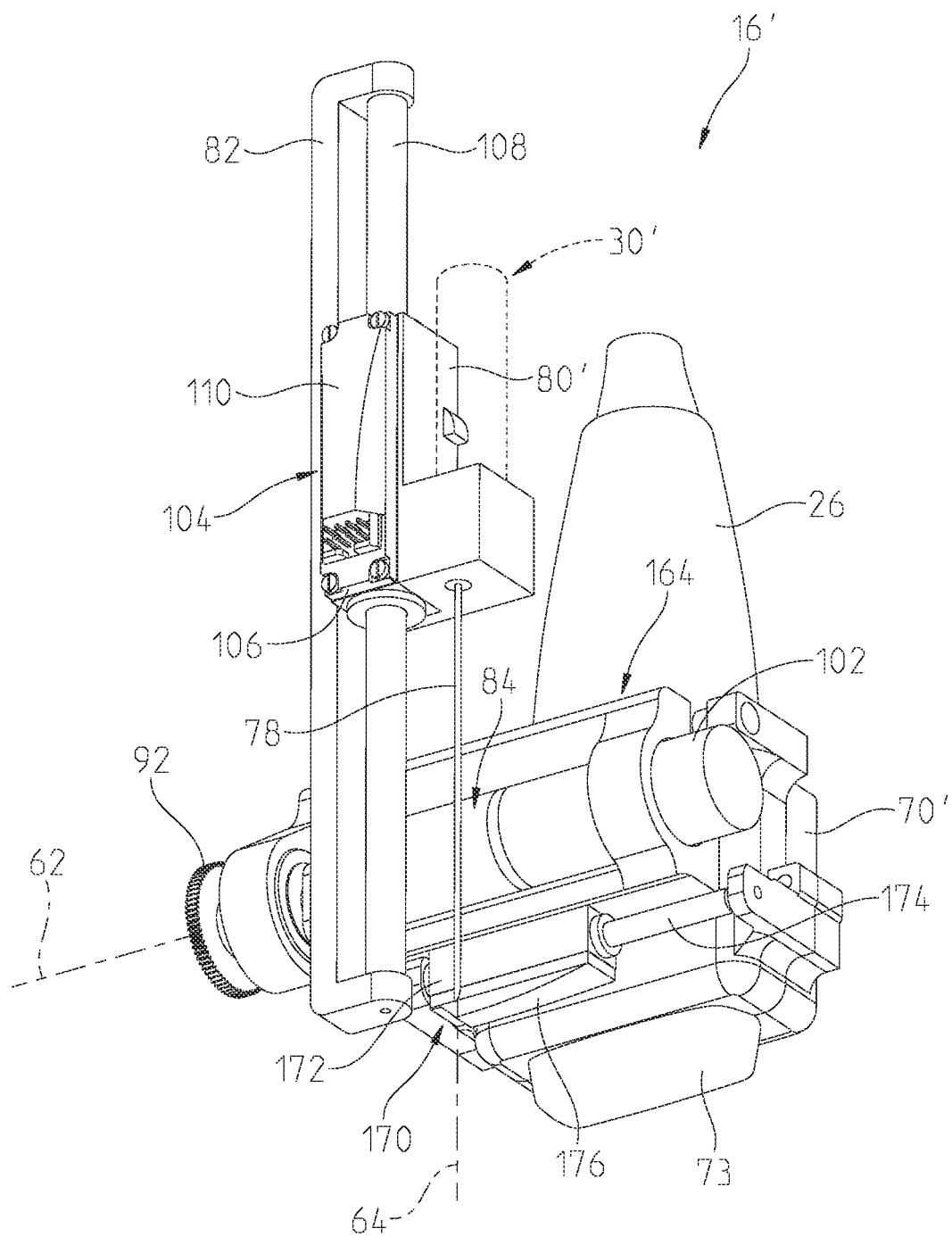
FIG. 14 is a front perspective view of a further illustrative delivery system of FIG. 1.
Figure 15:
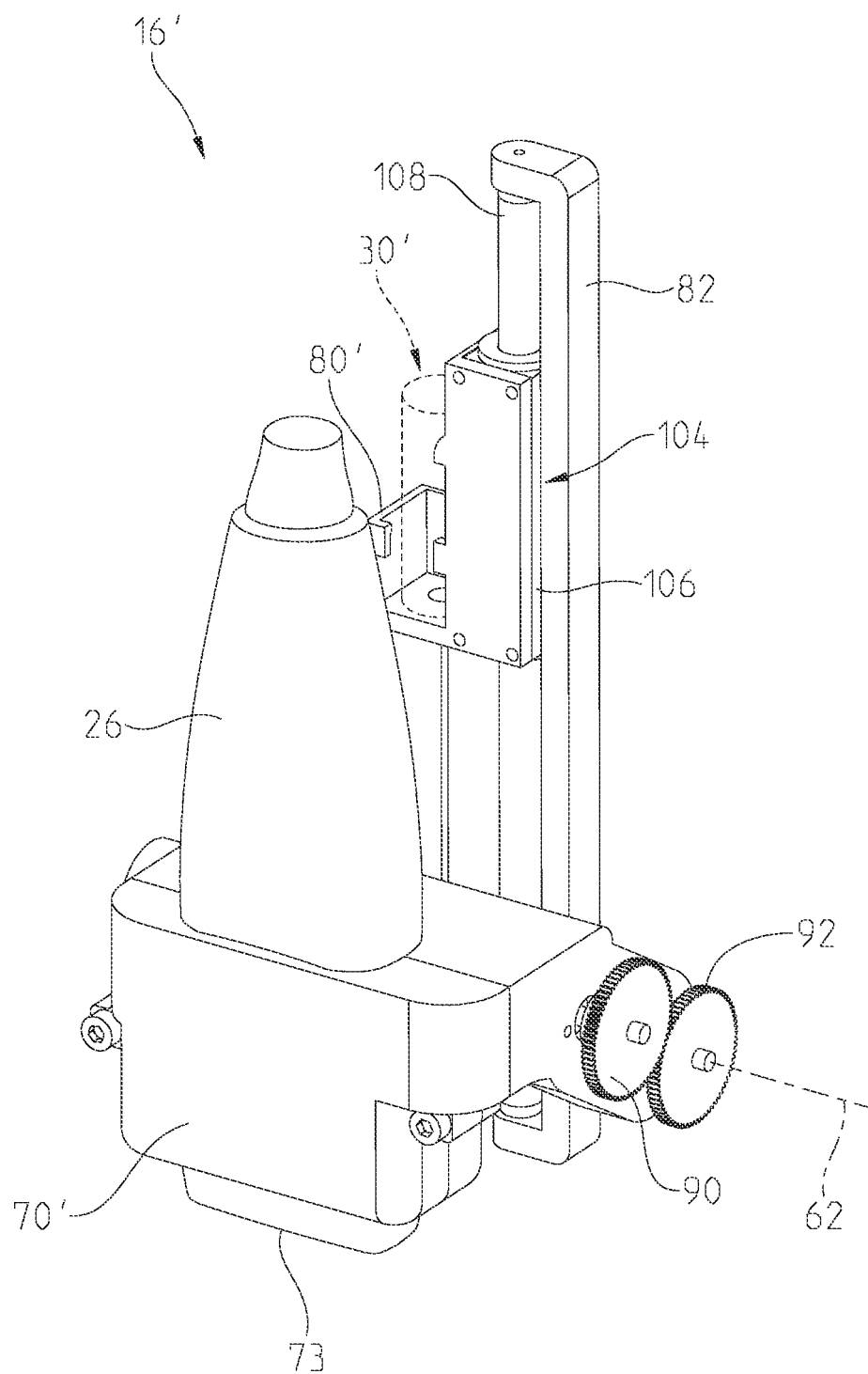
FIG. 15 is a rear perspective view of the delivery system of FIG. 14.
Figure 16:
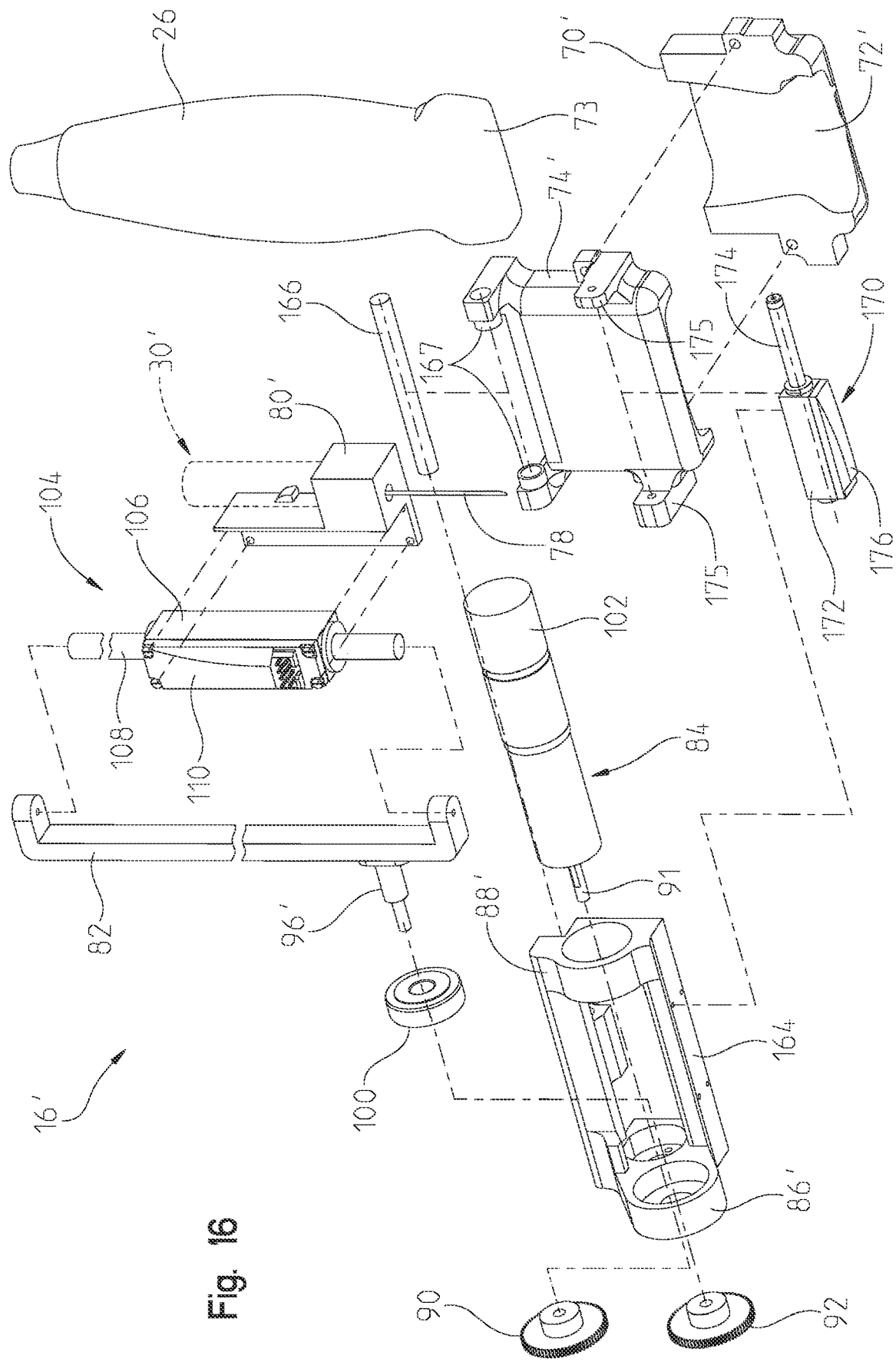
FIG. 16 is a front exploded perspective view of the delivery system of FIG. 14.
Figure 17:
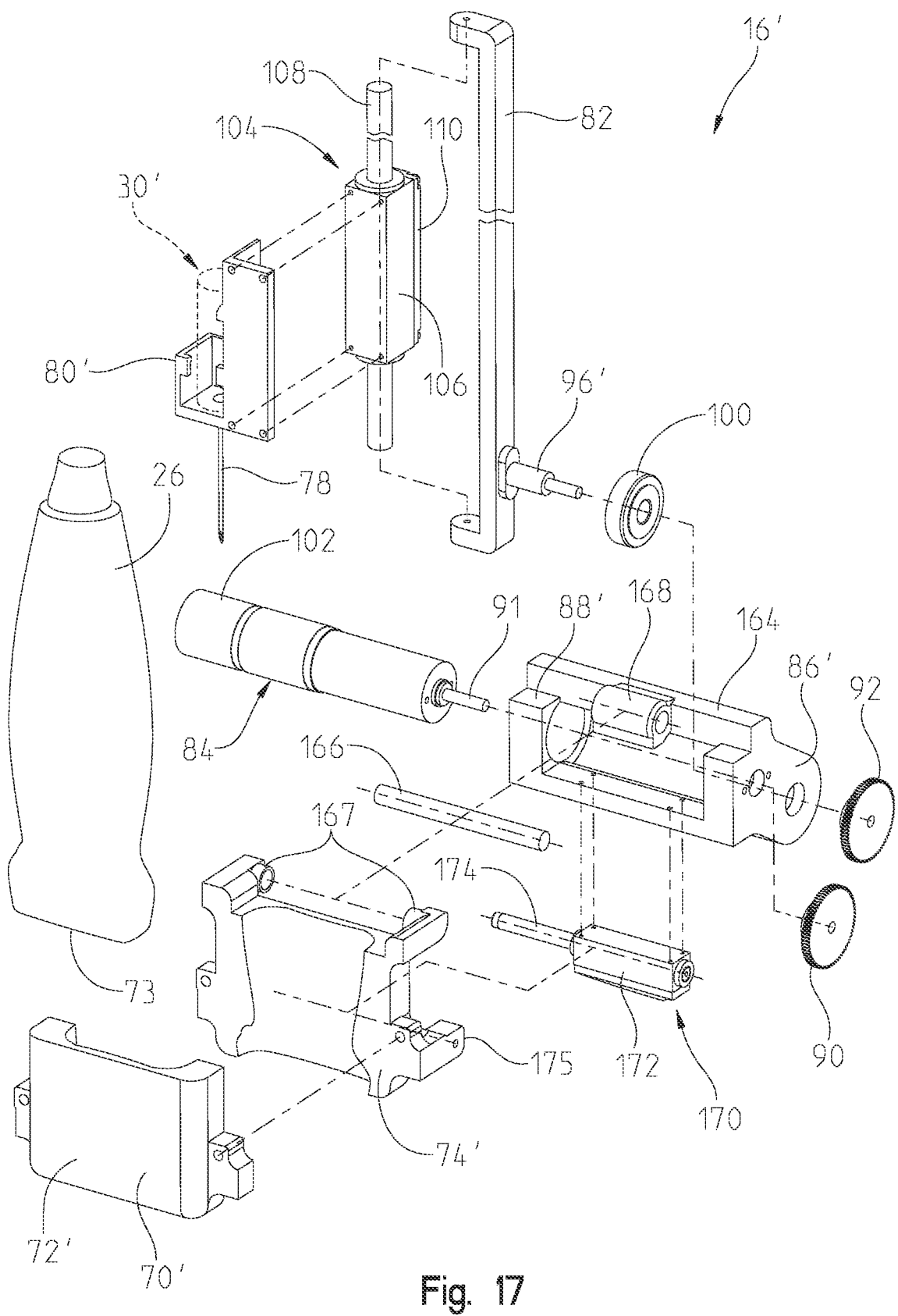
FIG. 17 is a rear exploded perspective view of the delivery system of FIG. 14.
Figure 18:
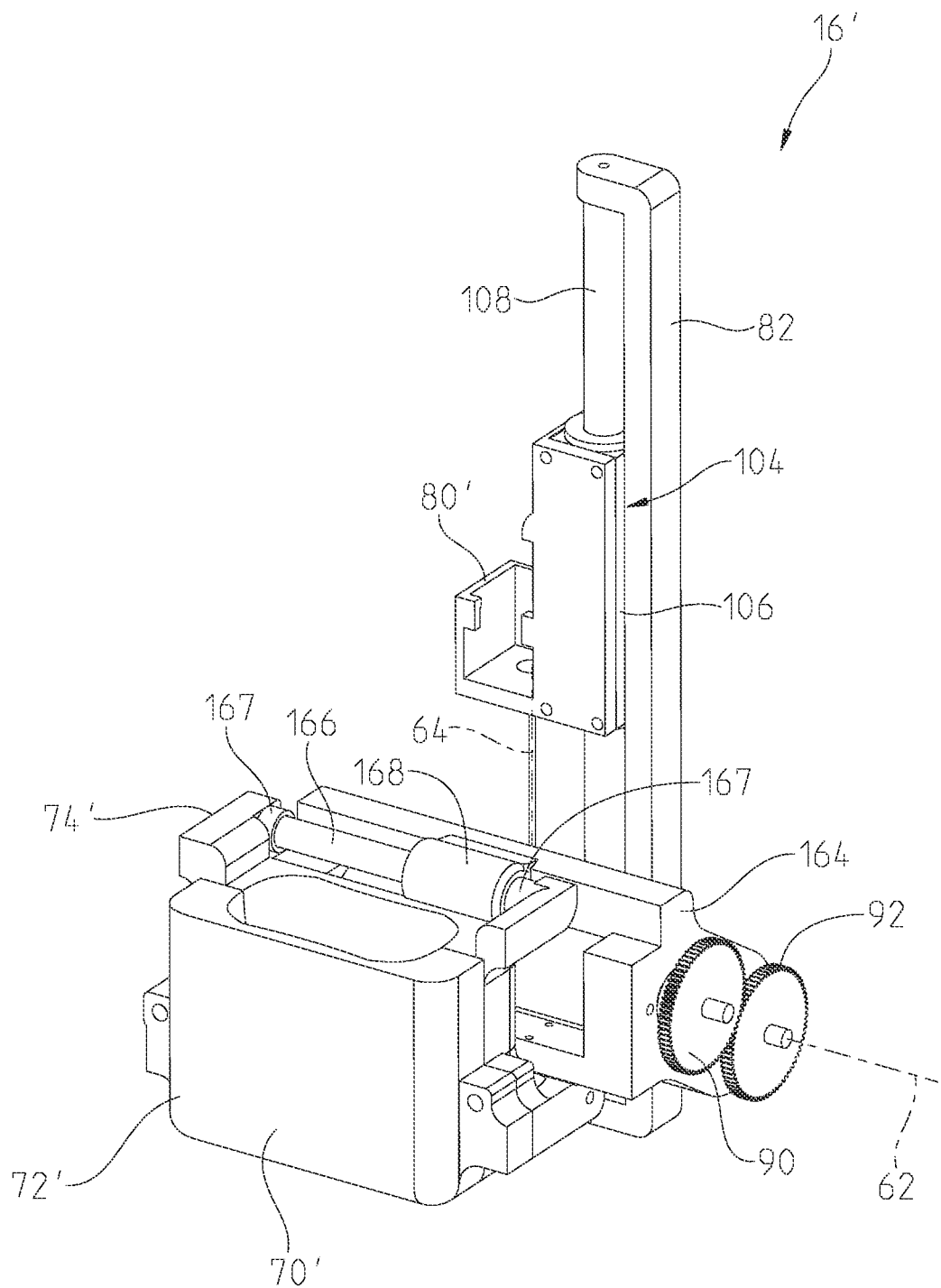
FIG. 18 is a partial rear perspective view of the delivery system of FIG. 14.

An alternative method of providing a command interface is through the use of the specially designed joystick 56 having input buttons 160a, 160b, 162a, and 162b (FIGS. 3, 12 and 13). In the illustrative embodiment, buttons 160a and 160b are directional buttons configured to rotate the needle 78 in opposite directions about the x-axis 62 by controlling the motor 84. Also in the illustrative embodiment, buttons 162a and 162b are start and out buttons configured to translate the needle 78 in opposite directions along the z-axis 64 into and out of the target vein 60. In addition, voice and signal recognition techniques may be used to send commands to the high level processor 18.

Illustratively, the system 10: 1) incorporates an appropriate ultrasound imaging probe 26 with the mechanical guidance mechanism to provide consistent registration of the ultrasound image with the coordinates of the robotic guidance, 2) includes interface software to transfer the information from the targeting imaging to the guidance system, and 3) defines an optimal human machine interface 22.

In operation, the ultrasound probe 26 may be received within the joystick 56. The operator searches for the area of interest in the same way that he uses to work with ultrasound probe 26. The needle 78 and the ultrasound probe 26 move together. Once the target vein 60 is found, the operator activates the moving mechanism by using the buttons 160, 162.

Figure 19:
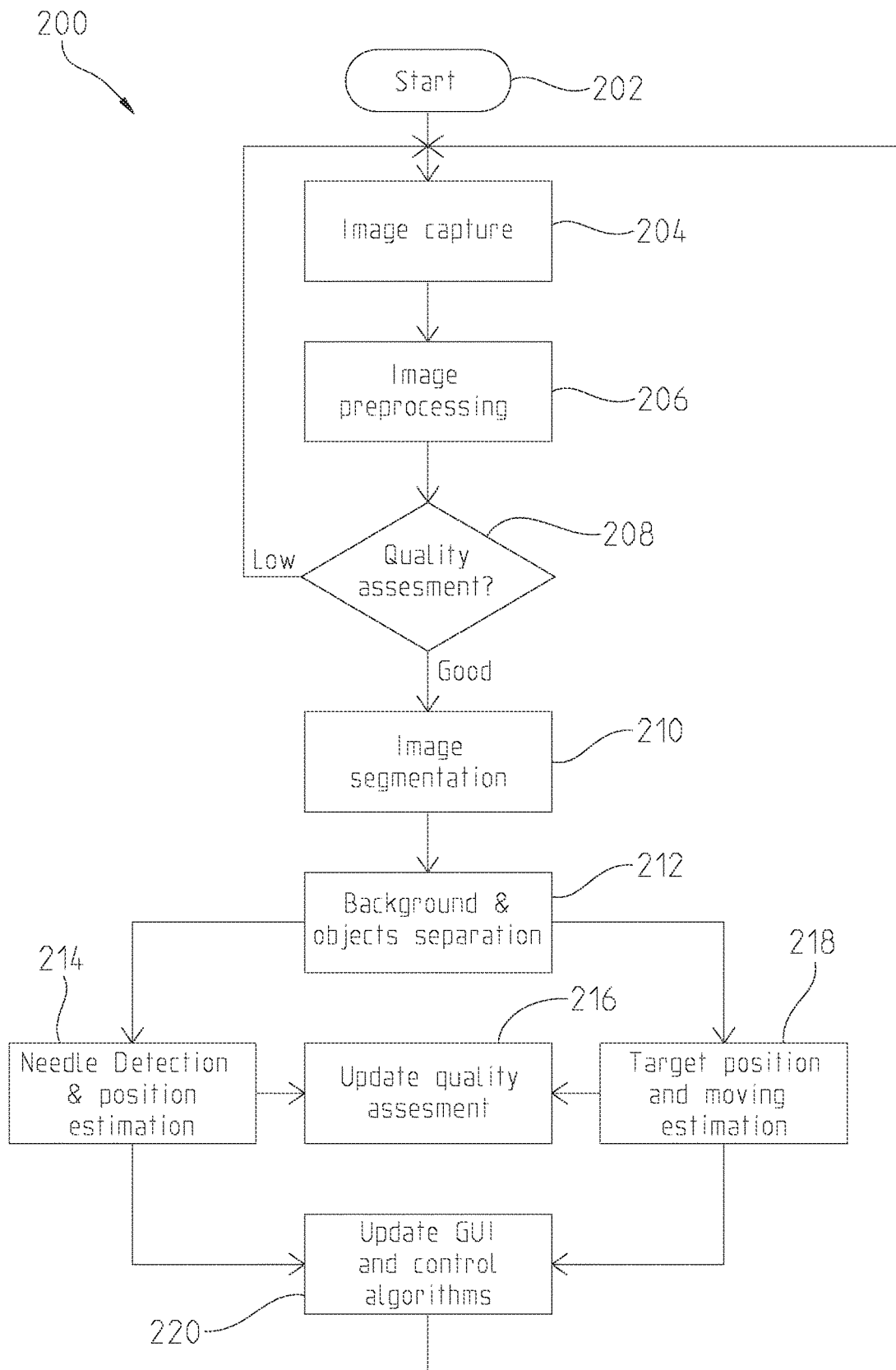
FIG. 19 is a flowchart of an illustrative image processing method of the device of FIG. 1.

A general flowchart diagram of the image processing module or subroutine 200 implemented by the central processing unit 24 is shown in FIG. 19. The process begins at block 202 by activation of the system 10 by the operator. The ultrasound (US) image 33 is captured by the frame grabber 20 and processed in real-time by the image processing module 200.

At block 206, the image preprocessing module 250 (FIG. 20) is configured to remove noise and automatically calibrate the ultrasound images. Beginning at block 252, the ultrasound data (images) are received. These ultrasound images may be perturbed by a multiplicative noise called speckle, due to the coherent nature of the scattering phenomenon. Speckle reduction filters may be required to optimize the images exploitation procedures. The results of speckle filters may vary from one sensor and one wavelength to another; therefore, no generic de-speckling algorithm exists.

Speckle noise suppression techniques can be divided into two main categories. The first approach is to average several looks or images acquired of the same scene, which is called multi-look processing or super-resolution. If several images are acquired from the same scene and then averaged, the speckle noise will be reduced due to its random nature, while the observed scene will not be degraded. Additional details of such an approach are detailed in V. S. Frost, J. A. Stiles, K. S. Shanmugan, and J. C. Holtzman, "A Model for Radar Images and Its Application to Adaptive Digital Filtering of Multiplicative Noise," Pattern Analysis and Machine Intelligence, IEEE Transactions on, vol. PAMI-4, pp. 157-166, 1982, the disclosure of which is expressly incorporated herein by reference.

The second speckle noise suppression technique is based on filtering the speckle noise after the images are formed. The simplest filters that can be applied on the speckled image are low-pass (Box) and median filters. The low-pass filter locally averages the image and by doing so removes the speckle. It is useful when the areas of interest in the image are homogeneous, but has very poor performance at edges and with high frequency information textures. The median filter, on the other hand, preserves the image edges, but can remove small area objects.

Contrary to the standard filters, the adaptive filters take local image information into consideration while carrying out the filtration process. Adaptive filters can reduce speckle noise in homogeneous areas while preserving texture and high frequency information in heterogeneous areas.

The design of each speckle suppression filter is based on different criteria and parameters, and the performance of each speckle filter may vary from one sonar to another; therefore, no generic de-speckling algorithm exists. Consequently, selection of the right de-speckling filter for a specific environment and sensor is a difficult task.

In order to deal with the noise reduction problem, the first stage speckle noise suppression is carried out at block 254 using an adaptive Frost filter with a n×n (17×17) kernel size. Then at block 256, local image histogram entropy is calculated in a m×m (9×9) pixel neighborhood to provide an informational measure. At a final stage of block 258, the hysteretic threshold of the entropy takes place.

The Frost filter estimates the observed scene by convolving the acquired image with an adaptive kernel, which changes its properties according to the local image statistics. The process can be defined by the following equation:

$$\hat{R}(x,y) = I(x,y) * m(x,y) \tag{1}$$

where (x,y) is the image spatial coordinates, I is the acquired image, is the estimated scene, and m(t) is adaptive kernel defined by:

$$m(x, y) = \frac{e^{-KC_I^2(x,y)|d|}}{\sum e^{-KC_I^2(x,y)|d|}}, C_1(x, y) = \frac{\sigma_I(x, y)}{\bar{I}(x, y)} \tag{2}$$

where K is the dumping factor (between 0.1 and 1), $|d|=|x-x_0|+|y-y_0|$ is the distance of the pixel from the kernel center. $C_I(x,y), \sigma_I(x,y)$ and $\bar{I}(x,y)$ are the image variation, standard deviation and mean in the filter area.

Segmentation of ultrasound images can be very complex, different obstacles with different echo return levels can exist in the single image. Local image histogram entropy-based segmentation provides outstanding results both in detection of obstacles and rejecting the seabed returns. Additional details of such segmentation are provided in C. I. Chang, Y. Du, J. Wang, S. M. Guo, and P. D. Thouin, "Survey and comparative analysis of entropy and relative entropy thresholding techniques," Vision, Image and Signal Processing, IEE Proceedings—, vol. 153, pp. 837-850, 2006, the disclosure of which is expressly incorporated by reference herein.

The local histogram entropy is based on the Shannon Theorem and was previously used for segmentation of optical images. Entropy is the measure of the information content in a probability distribution, and can be defined by the following formula:

$$E_1(x, y) = \sum_{i=0}^{N_{bins}} \frac{p(i)}{N_{bins}} \cdot \log\left(\frac{p(i)}{N_{bins}}\right) \tag{3}$$

where p(i) is the value of the particular bin of the $N_{bins}$ local histogram of the image in the N×N pixel neighborhood at (x,y) coordinates. Additional details of local histogram entropy are provided in A. S. Abutaleb, "Automatic thresholding of gray-level pictures using two-dimensional entropy," Computer Vision, Graphics, and Image Processing, vol. 47, pp. 22-32, 1989, the disclosure of which is expressly incorporated by reference herein.

Figure 21:
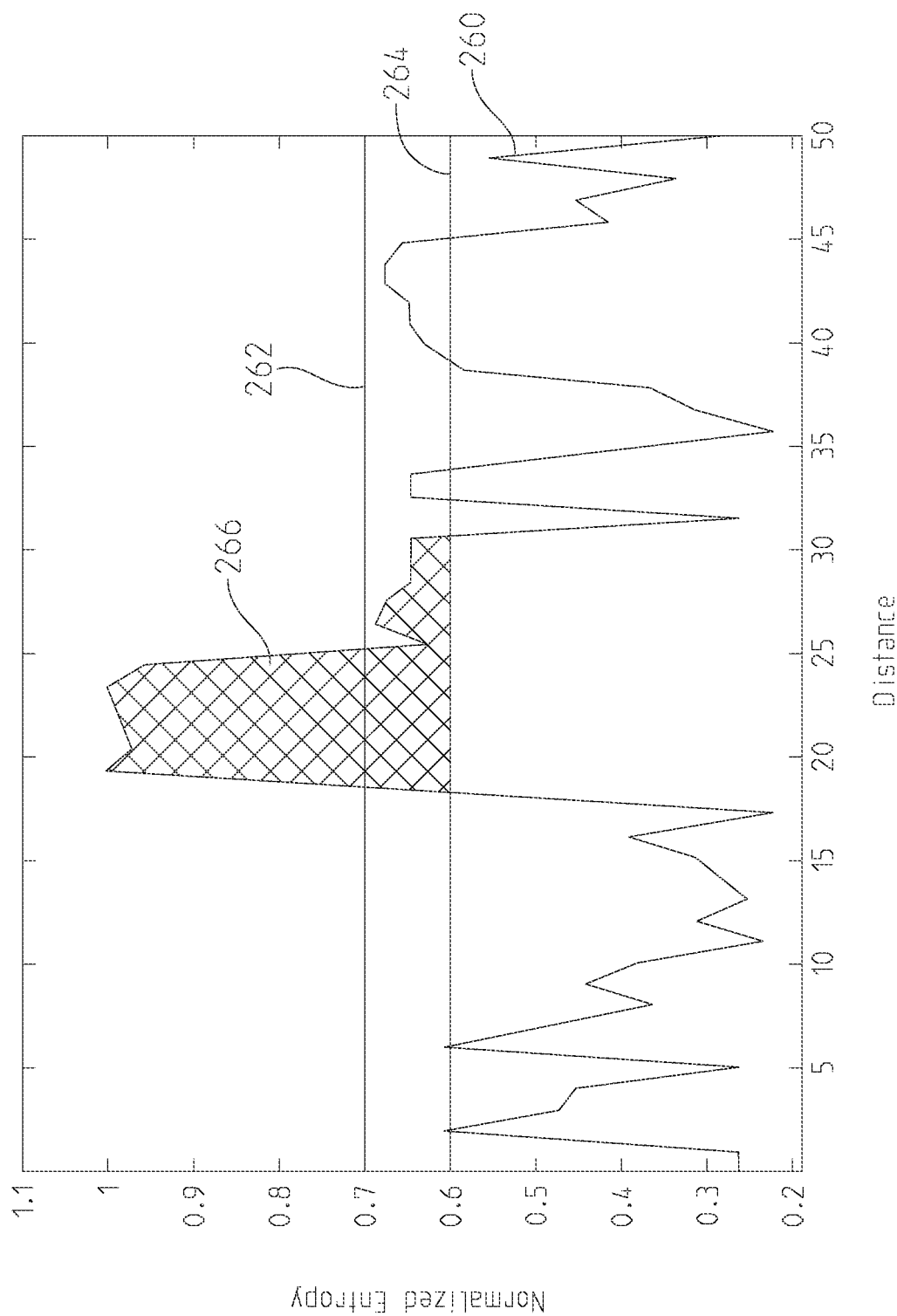
FIG. 21 is a chart of an illustrative hysteretic threshold.

A hysteretic threshold is then applied on the entropy result. A hysteretic threshold uses two different thresholds. The first high-level threshold selects the parts of the image that are to be treated as objects, while the second low-level threshold selects the areas that will be treated as an object only if they are connected by four-connectivity to the pixels that are above a high-level threshold. 70% and 60% of the maximum entropy level were used as high and low thresholds, respectively as can be seen in FIG. 21. The first interest of this algorithm is to discard middle value peaks not connected to high entropy regions and ignore the noise.

FIG. 21 illustrates the hysteretic threshold, where line 260 indicates the normalized entropy from one of the ultrasound image beams. Lines 262 and 264 indicate high and low level thresholds, while the shaded area 266 is the region that was selected.

Next, at block 270 the image map might be thresholded and converted to an binary image based on the rationality that noise is more apparent in the tissue regions than in the needle and target (vein) areas. Optionally, the binary image is smoothed and refined using morphological operators such as opening and closing. A blob filter might is used to remove residues of tissue in vein areas.

The second task of the image preprocessing module 250 is to automatically calibrate the system according to the ultrasound depth working range. The module 250 searches for the scale markers provided in the ultrasound image (see mark points in FIG. 21) at block 272. At block 274, the module 250 determines determine the position of the markers in the image and estimates the scale. Alternatively, it can use OCR algorithms to read the information written in the screen.

Optionally, the scale information might be obtained by either analyzing the image, by using a communication channel such as RS-232, Ethernet, wire or wireless. Also, the information might be provided directly by the operator through the human machine interface 22.

The results provided by the image preprocessing module 250 are feed into the quality assessment (QA) module at block 208 which evaluates the validity of the information provided. The task of the QA module is to monitor the behavior of the processing algorithms and detect faults and misbehaviors at any stage. For example, the QA check the sample frequency of the ultrasound sensor and if the signal-to-noise ratio is enough to allow the image processing task. If the quality is low, then the process returns to block 204.

With further reference to the quality assessment module, robot control involves much uncertainty, both for state (position) estimation, as well as prediction. There always exist the possibility of a malfunction the main objective of this module is to test possibility of faults or malfunctions to ensure a higher degree of safety.

Examples include: (1) the QA test quality of the US image by using features such as image histogram, edge detection frequency is possible to know if the quality of the image is suitable; (2) fail to receive the US image at a stable frame rate (i.e. 30 f/s), (3) position markers are not available, (4) unknown areas in the US image and inability of the system to classify significant areas (greater than 20%) of the image might indicate that the US sensor is not applied correctly, and (5) due to noise or movement the tracking algorithms might be unable to follow either the target, the needle or both. This might indicate that the US sensor is not stable.

The operator may be informed at every stage of the QA by a simple color indication on the GUI. For example, green designates "OK", yellow designates "unstable behavior", and red designates "major fault". In case of red status, the system will be disabled automatically.

Figure 22:
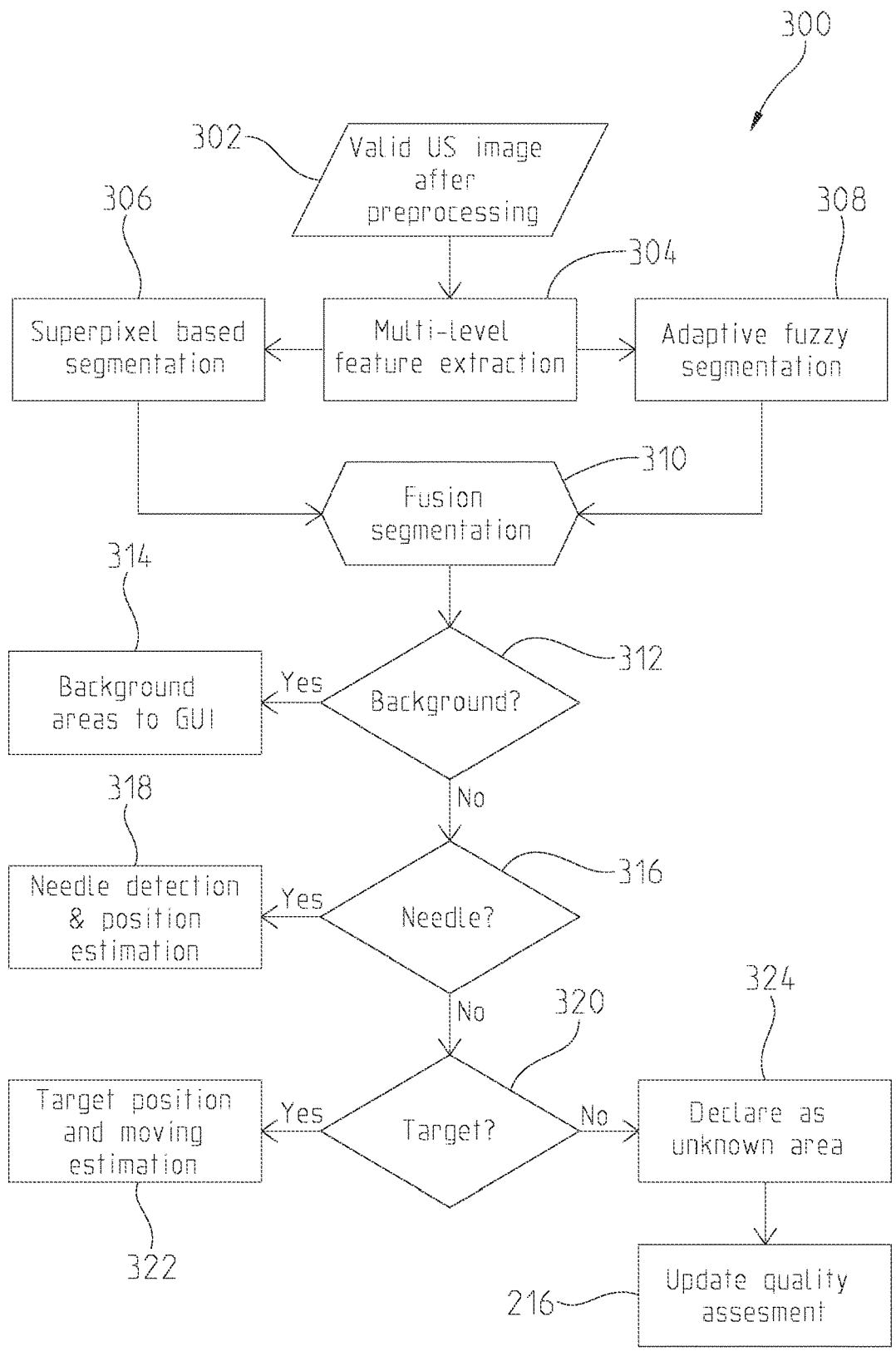
FIG. 22 is a flowchart of an illustrative background and objects segmentation module.

Returning to the image processing module 200 of FIG. 19, once the ultrasound raw data is successfully processed the information is illustratively forwarded at block 212 to the background and object segmentation (BOS) module 300 (FIG. 22).

Image segmentation is the technique of decomposing an image into meaningful parts, or objects. It results in a segmented image, where each object is labeled in a way that facilitates the description of the original image so that it can be interpreted by the system that handles the image. This implies that the image segmentation process plays a key role in any automated image understanding system. Additional details of illustrative image segmentation are provided in N. R. Pal and S. K. Pal, "A review on image segmentation techniques", Pattern Recog., vol. 26, pp. 1277-1294, 1993, the disclosure of which is expressly incorporated herein by reference.

In general, the classification of an image's pixels as belonging to one of the "objects" (i.e. classes) composing the image is based on some common feature(s), or resemblance to some pattern. Generally, in order to determine which are the features that can lead to a successful classification, some a priori knowledge or/and assumptions about the image are required. It is due to this fact that the best results are obtained by segmentation algorithms "tailored" for specific applications (but which will perform poorly on applications other than the one they were designed for).

The majority of the segmentation algorithms produce two level, or "background and object" segmentation. While such a result is appropriate for some of the 'classical' image processing applications such as the automatic image analysis, it is not satisfactory for applications dealing with more complex scenes such as US images, where several objects have to be detected.

Image segmentation is primarily used to identify the boundaries and objects in given US images. More importantly, image segmentation is the process of giving a label to every pixel in an image such that pixels with the similar label share same characteristics. The meaning of context is the information of the area which are given by single pixel, and that single pixel will give the information of the surrounding pixel also. The result of segmentation is the set of segments that consist of the important detail of that image, or a set of contours extracted from the image. Generally the pixels of a particular region are similar with respect to some characteristic such as color, intensity, or texture. US images are differentiate the place by roughness and intensity level, which result in different in brightness and textures. As US images presents a high variability there is no insurance that any segmentation method or set of features will produce reliable results all the time. Therefore, the processor 18 illustratively employs two robust segmentation methods: Superpixel based segmentation at block 306, and Fuzzy C means (FCM) at block 308, together with a relative large number of features obtained at different scales.

With reference to block 306, TurboPixels are used to extract superpixels from an image, in which one superpixel is roughly uniform in texture and gray, so that the boundaries of regions are preserved. In order to encode gray, texture and spatial information into superpixels, we describe each superpixel j by a 7-dimensional wavelet feature vector F is the average wavelet value of all pixels in superpixel j across 3 layers. This feature is represented as the average location of all pixels in superpixel j. Additional details of superpixel based segmentation are provided in A. Levinshtein, A. Stere, K. N. Kutulakos, D. J. Fleet, S. J. Dickinson, and K. Siddiqfi, "TurboPixels: Fast superpixels using geometric flows," IEEE Transactions pattern, vol. 31, no. 12, pp. 2290-2297, December 2009, the disclosure of which is expressly incorporated herein by reference.

The FCM segmentation of block 308 employs the entropy features previously described and the pixel position to produce a segmentation map. The segmentation provided by both methods is then fuse into a single representation at block 310.

Each region is the labeled either as background at block 312, needle at block 316, target (either object or needle) at block 320, or unknown area at block 324. The background region is immediately sent to the GUI module at block 314, and the information used to enhance the image. Unknown areas are reported to the QA module at block 216, if the percentage of unknown areas is high a malfunction is reported. The needle and target areas are transfer to the respective tracking modules at blocks 318 and 322.

Returning to the image processing module 200, the needle detection and tracking module 350 (FIG. 23) at block 352 receives the region of interest (ROI) and features previously extracted at block 214. In addition the expected insertion trajectory is provided at block 354. Optionally, information concerning the needle size and form may be provided.

Upon receiving the insertion command the needle detection and tracking module 350 begins to follow up the needle position. The needle detection and tracking module 350 uses two sources of information: 1) motors position and 2) detection of the needle in the image. When the needle 78 is outside the body the position the motor encoders are the only source of information. After the needle 78 enters the ultrasound scanning area, the position is determined by both methods. This arrangement ensures a more robust and exact position determination.

The needle identification is performed by either an ADA-BOOST, Neural Network or an SVM based classifier at block 356. Once the needle 78 is successfully identified at block 358, the following features are illustratively extracted:
Position (centroid) in the image;
Area of the needle in pixels;
Perimeter of the needle in pixels.
Then the needle 78 is mapped into a global world coordinates according to equation (4).

$$\begin{bmatrix} x' \\ y' \end{bmatrix} = A(\varphi, \theta) \begin{bmatrix} x \\ y \end{bmatrix} + \begin{bmatrix} x_c \\ y_c \end{bmatrix} \quad (4)$$

Where x and y is local coordination, $x_c$ and $y_c$ is US sensor global coordinate, $\varphi$ is pitch angle, $\theta$ is yaw angle and $A(\varphi,\theta)$ is a transformation matrix defined by equation (5).

$$a = \begin{bmatrix} \cos(\varphi) \cdot \cos(\theta) & -\cos(\theta) \cdot \sin(\varphi) \\ \cos(\theta) \cdot \sin(\varphi) & \cos(\varphi) \cdot \cos(\theta) \end{bmatrix} \quad (5)$$

In order to reduce the influence of noisy measures, an adaptive Kalman filter is employed to estimate the position and velocity at block 362. The information is feed to the GUI at block 364, and to the delivery system controller at block 366.

With reference again to the image processing module 200 of FIG. 19, at block 218 the target detection and tracking module 400 (FIG. 24) receives the ROI and relevant features. The target identification is performed by either an ADABOOST, Neural Network or an SVM based classifier at block 404. Once the target is successfully identified the following features are illustratively extracted:
Position (centroid) in the image;
Area of the target in pixels;
Perimeter of the target in pixels.
Borders of the target
Contour of the target
Equations 4 and 5 as detailed above are employed to determinate the global position of the target. Shape algorithms are used to detect the target borders at block 410. Once the target is identified, an adaptive Kalman filter is employed to estimate the position and velocity at block 412. The information is then fed to the GUI at block 414, and to the delivery system controller at block 416.

With reference now to FIGS. 25-34, the illustrative graphical user interface (GUI) 150 is shown. The graphical user interface 150 is configured to permit the operator shall to continuously monitor and supervise the performance of the system 10 as a whole and quickly detect and understand possible problems.

The graphical user interface 150 is configured to reduce the workload on the system operator, reduce the amount of errors performed by the operator, reduce the amount of relevant or critical information either misunderstood or disregarded by the operator, and reduce the learning and training time and efforts required to qualify an operator.

The graphical user interface 150 uses information provided by different modules to reduce the amount of information/distraction the operator receives and focuses the operator's attention only to the needle insertion task. This may be attained by: removing the background area (FIGS. 25-28), enhancing the target region of interest, marking the needle trajectory, and updating the status of the system 10.

The illustrative graphical user interface 150 includes an ultrasound display screen or window area 450. The ultrasound window area 450 displays ultrasound images from the ultrasound system 12 and overlay graphics. The window area 450 includes a graphical representation of the target vein 60, illustratively inner and outer borders 452 and 454. A needle target or device mark 456 is illustrated by a cross-hair 458 received within a circle 460. A plurality of linearly aligned mark points 462 represent the center axis 71 of the ultrasound probe 26.

A Record input 464 allows for real time recording of the ultrasound window area 450. A Take a Picture input 466 takes a snapshot of the ultrasound window area 450. A STOP input 468 disables the system 10. A Zero Point input 470 allows for homing of the system 10 (e.g., returning the components, such as the motors 84 and 104 to a home or initial position). An Enable input 472 permits for activation of the motors 84 and 104. A Set Joystick Buttons input 474 permits the operator to reconfigure the functionality of the joystick buttons 160a, 160b, 162a, 162b.

An Adjust the Speed input 476 permits the operator to set the penetration speed of the needle 78. A Chose Joystick input 478 allows the operator to select between different types of joysticks 56. FRONT MODE and SIDE MODE inputs 480 are flags to inform the processor of how the ultrasound probe 26 is mounted.

A numeric keypad 482 permits the operator to send commands to the processor. A coordinate display window 484 displays x and y coordinates of the needle target 456. An informational display window 486 is configured to display messages to the operator, such as for debugging purposes.

An alternative means of providing command interface is through the use of the specially designed joystick 56 (FIGS. 12 and 13). Once the system 10 is set, all functions may be activated from the joystick 56. Buttons 160 allow the operator to move and set the target by moving the red cross-circle to the required area. Buttons 162 allow the operator to cause the needle 78 to penetrate the target vein 60, and withdraw from the target vein 60.

The target may be determined either:

Manually—the operator search for the target and set the cross—circle in the desired position; or Automatically—using the tracking algorithms the system suggest a possible (optimum) target position to the operator. The operator must confirm the selection.

Figure 20:
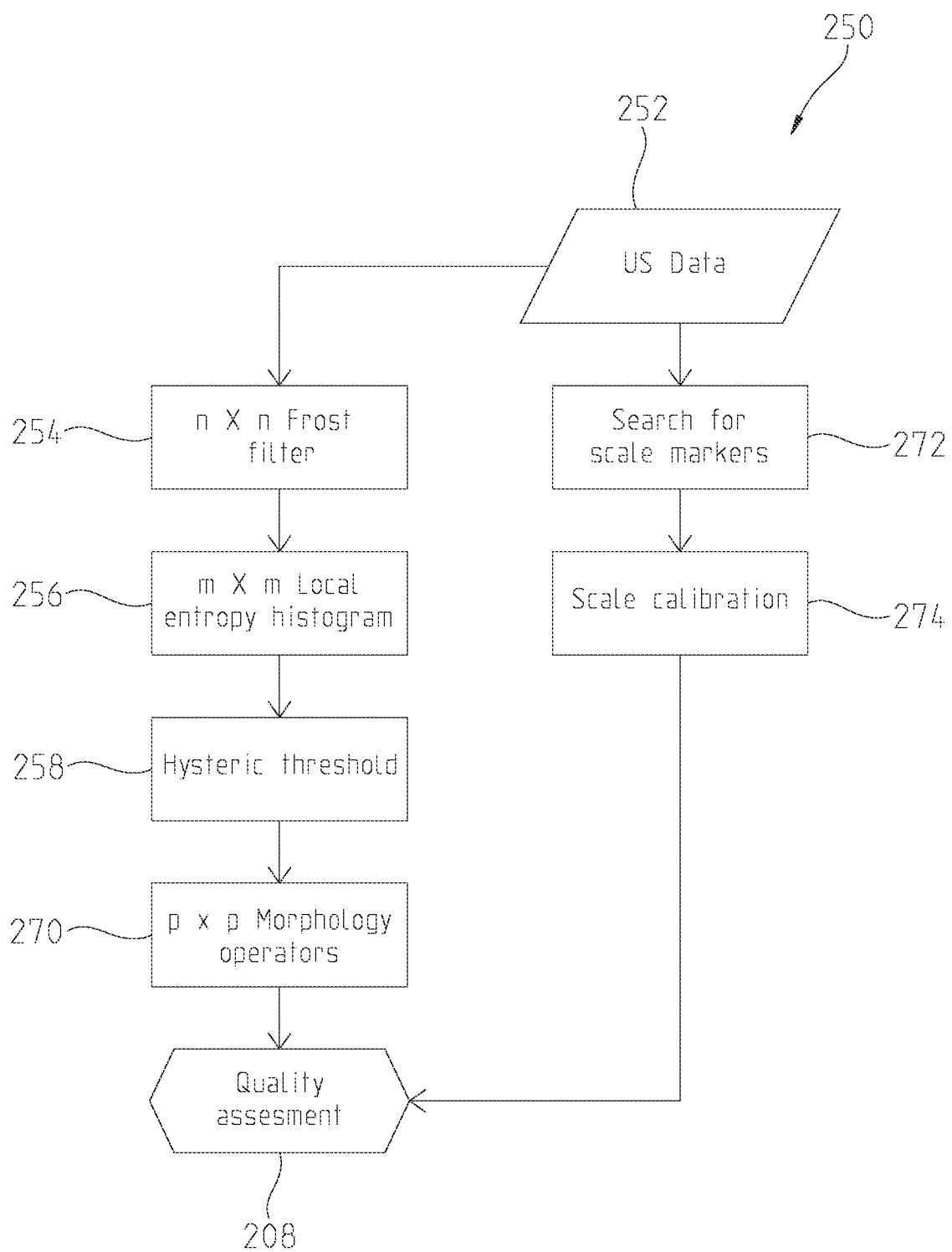
FIG. 20 is a flowchart of an illustrative image preprocessing module.
Figure 26:
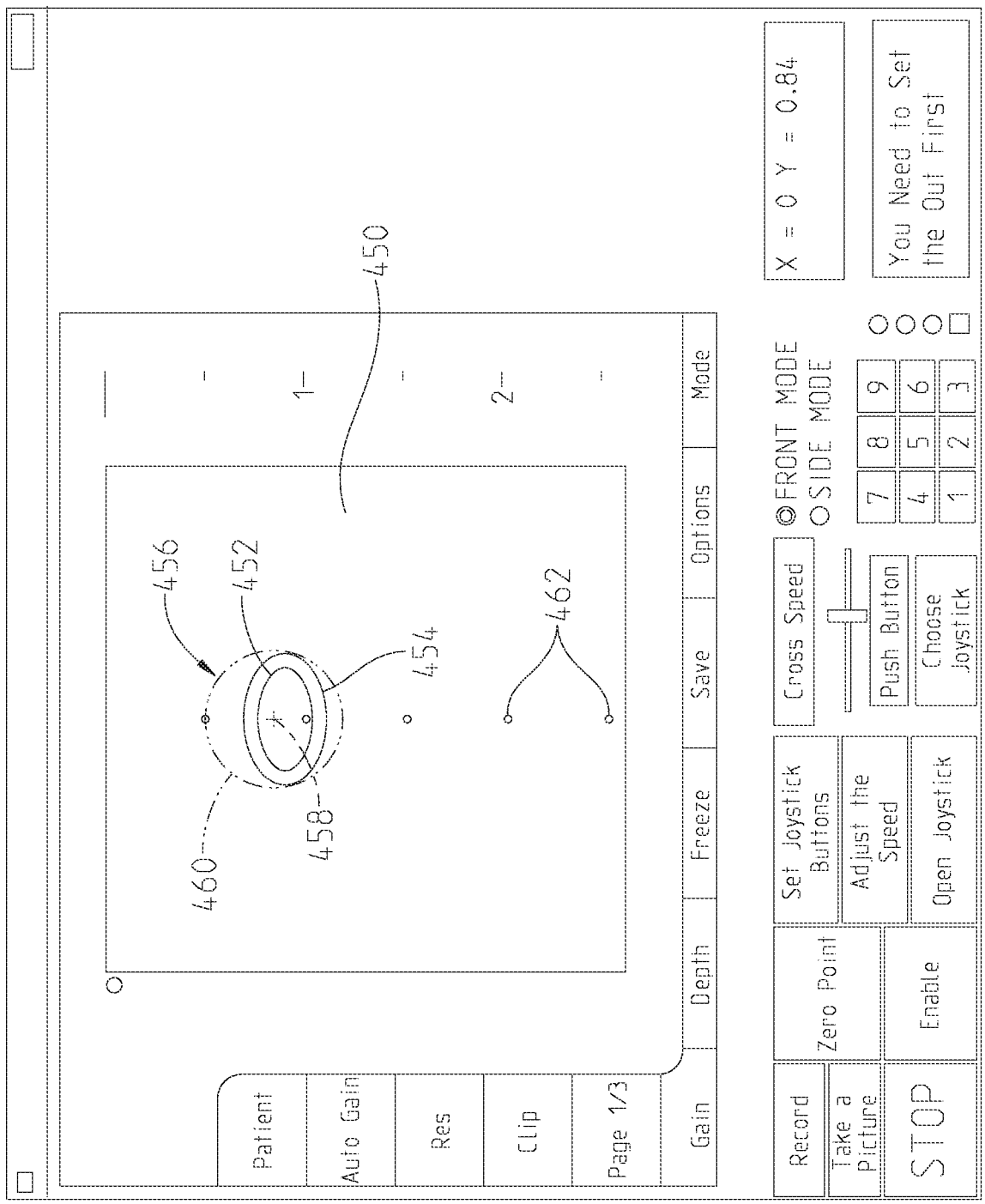
FIG. 26 is an illustrative view of the graphical user interface of FIG. 25, showing a processed ultrasound image.

FIGS. 25-28 illustrate operation of the background and object segmentation (BOS) module 300 on the ultrasound window area 450 of the graphical user interface 150. FIG. 20 illustrates the original ultrasound image received from the ultrasound system 12 with the ultrasound probe 26 in the front configuration. FIG. 26 illustrates the ultrasound image after processing by the background and object segmentation (BOS) module 300, where background clutter has been removed and the image enhanced. The needle target 456, including cross-hair 458 received within circle 460, identifies the projected trajectory of the needle 78.

Figure 28:
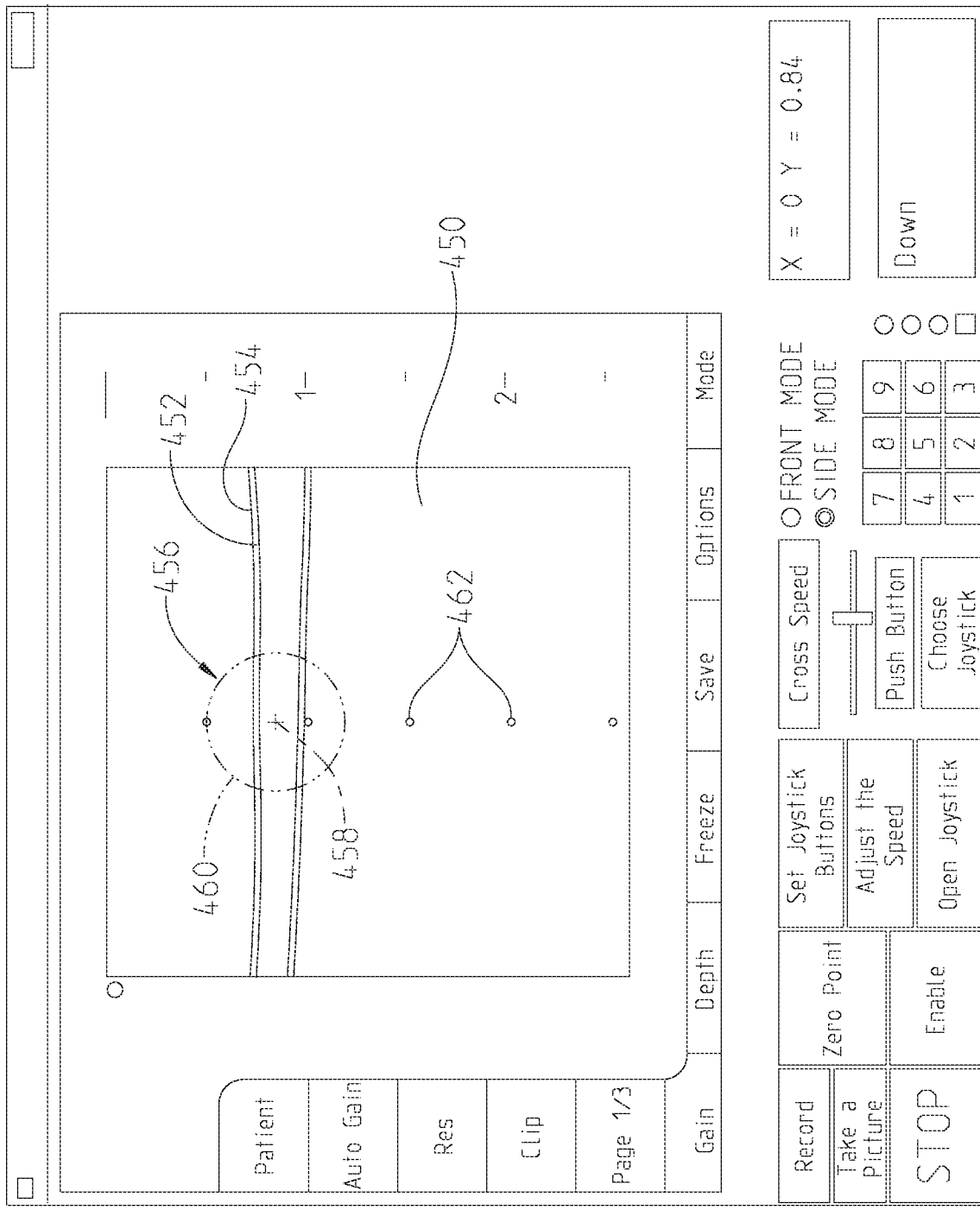
FIG. 28 is an illustrative view of the graphical user interface of FIG. 27, showing a processed ultrasound image.

FIG. 27 illustrates the original ultrasound image received from the ultrasound system 12 with the ultrasound probe 26 in the side configuration. FIG. 28 illustrates the ultrasound image after processing by the background and object segmentation (BOS) module 300, where background clutter has been removed and the image enhanced. The needle target 456, including cross-hair 458 received within circle 460, identifies the projected trajectory of the needle 78.

Figure 29:
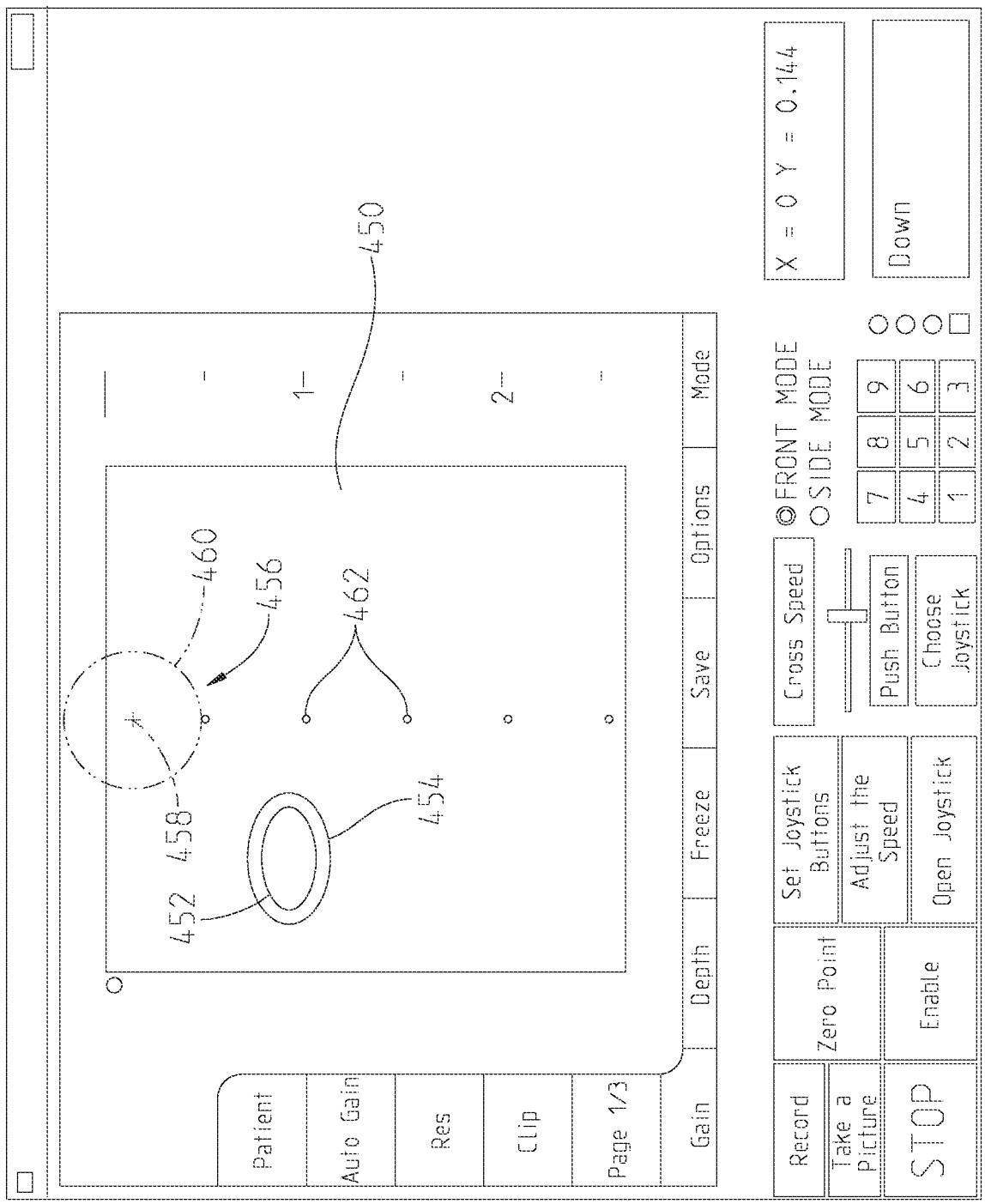
FIG. 29 is an illustrative view of the graphical user interface of FIG. 25, wherein the target vein is located left of the ultrasound sensor central axis.
Figure 30:
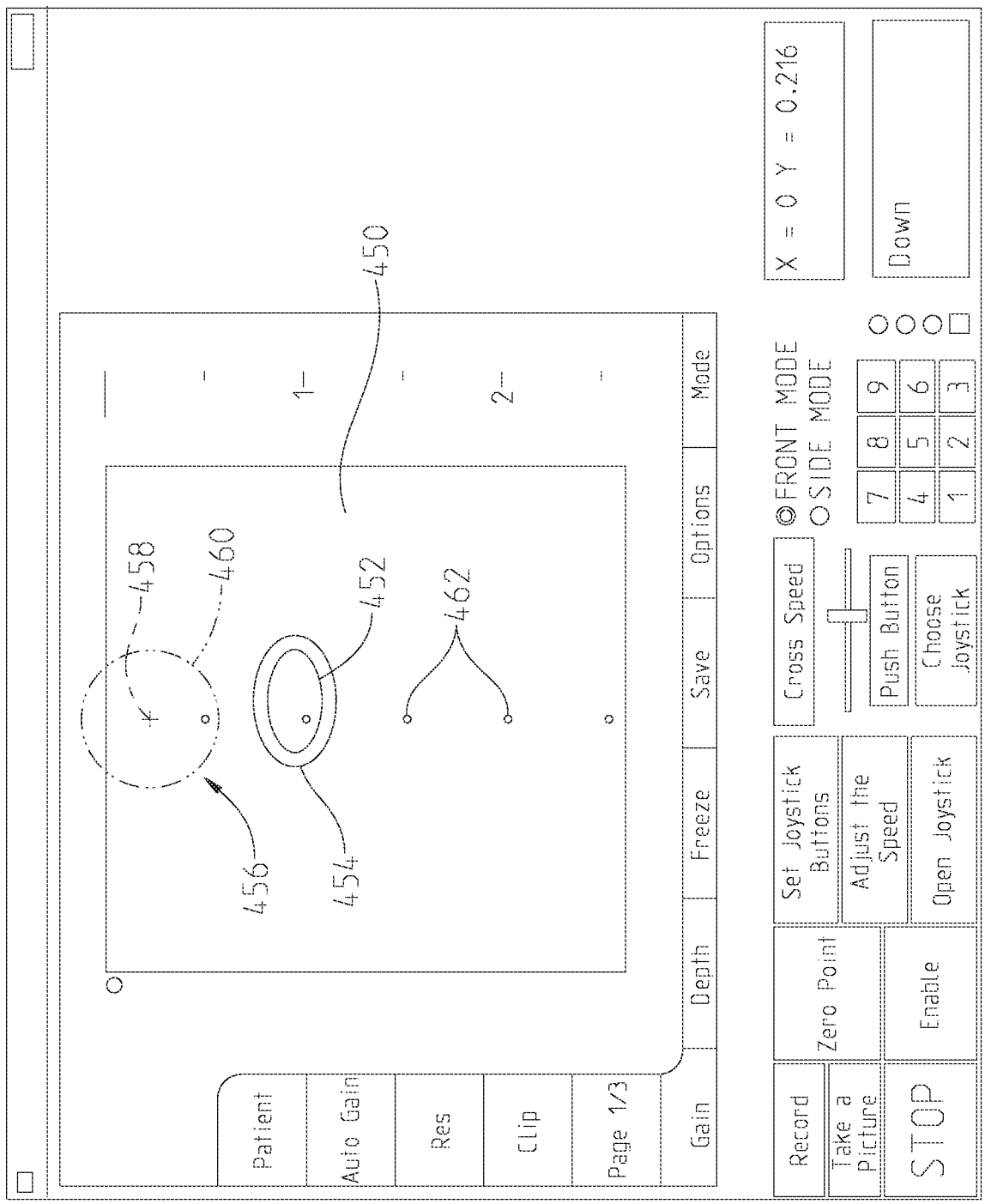
FIG. 30 is an illustrative view of the graphical user interface of FIG. 29, wherein the target vein is on the ultrasound sensor central axis.

FIGS. 29-32 show different stages of the tracking and target selection process as displayed on the graphical user interface 150. In FIG. 29, the target vein 60 represented by the borders 452 and 454 is located to the left ultrasound probe axis represented by mark points 462. The operator may then move the dispenser and control unit 16 to the right such that the target vein 60 represented by borders 452 and 454 is aligned with the ultrasound probe axis represented by mark points 462 as shown in FIG. 30.

Figure 31:
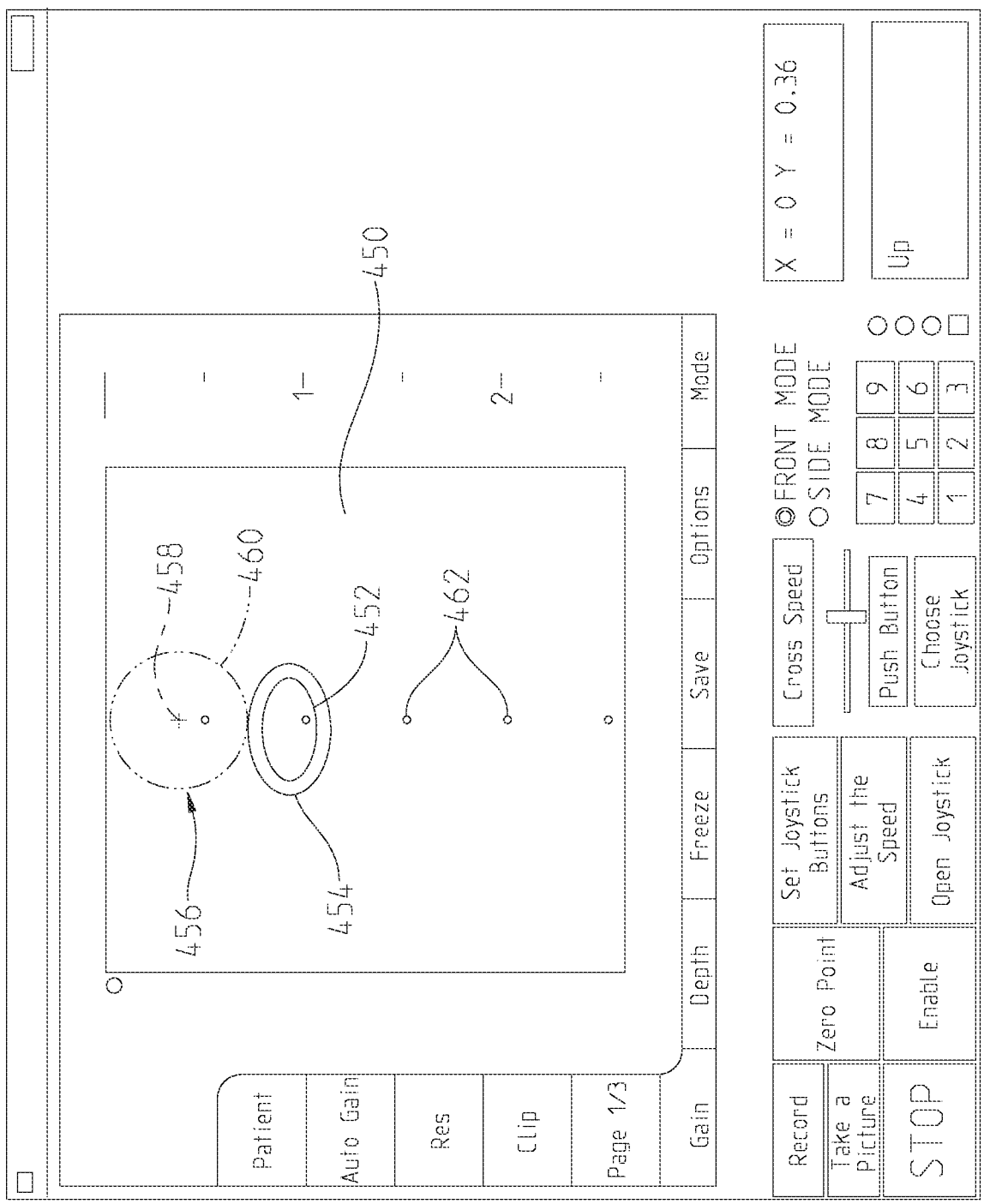
FIG. 31 is an illustrative view of the graphical user interface of FIG. 29, wherein the target vein is on the ultrasound sensor central axis and the needle cross-circle is moving toward the target vein.
Figure 32:
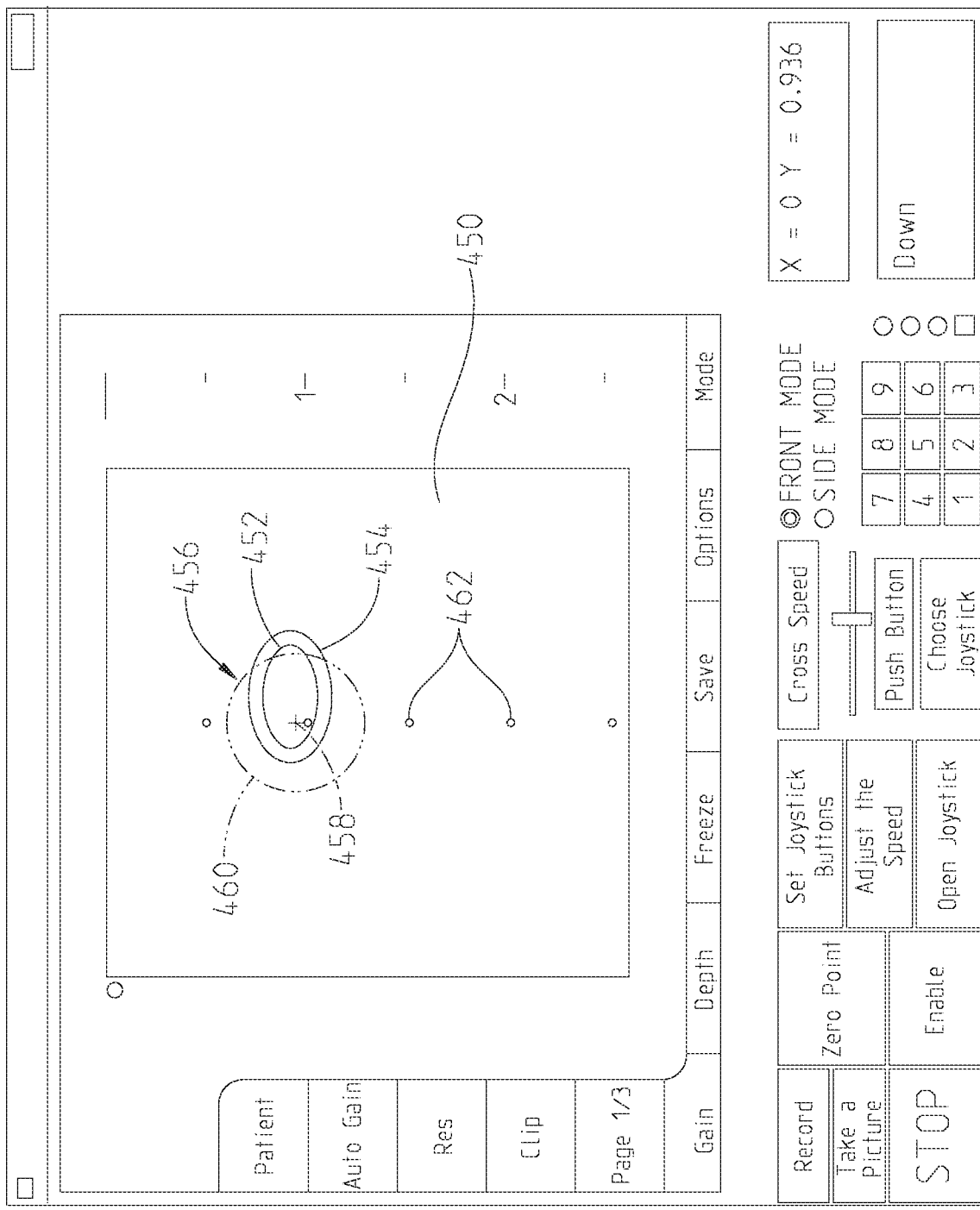
FIG. 32 is an illustrative view of the graphical user interface of FIG. 29, wherein the needle cross-circle marks the target vein.

Once the operator is satisfied with the selection, he activates the insertion process by pressing the Start button 162a on the joystick 56. The target position is sent to the path planner 36 which searches for the optimal needle trajectory and sends the information to the control unit. First, the control unit sets the dispenser to the pre-defined insertion angle. Then the linear motor 104 is activated and the needle 78 inserted. As the motor 84 of the dispenser and control unit 16 rotates the needle 78 toward the target vein 60, the needle target 456 moves toward the borders 452 and 454 as shown in FIG. 31. FIG. 32 shows the needle target 456 aligned with the borders 452 and 454, where the cross-hair 458 is positioned within the inner border 452 of the target vein 60.

Figure 33:
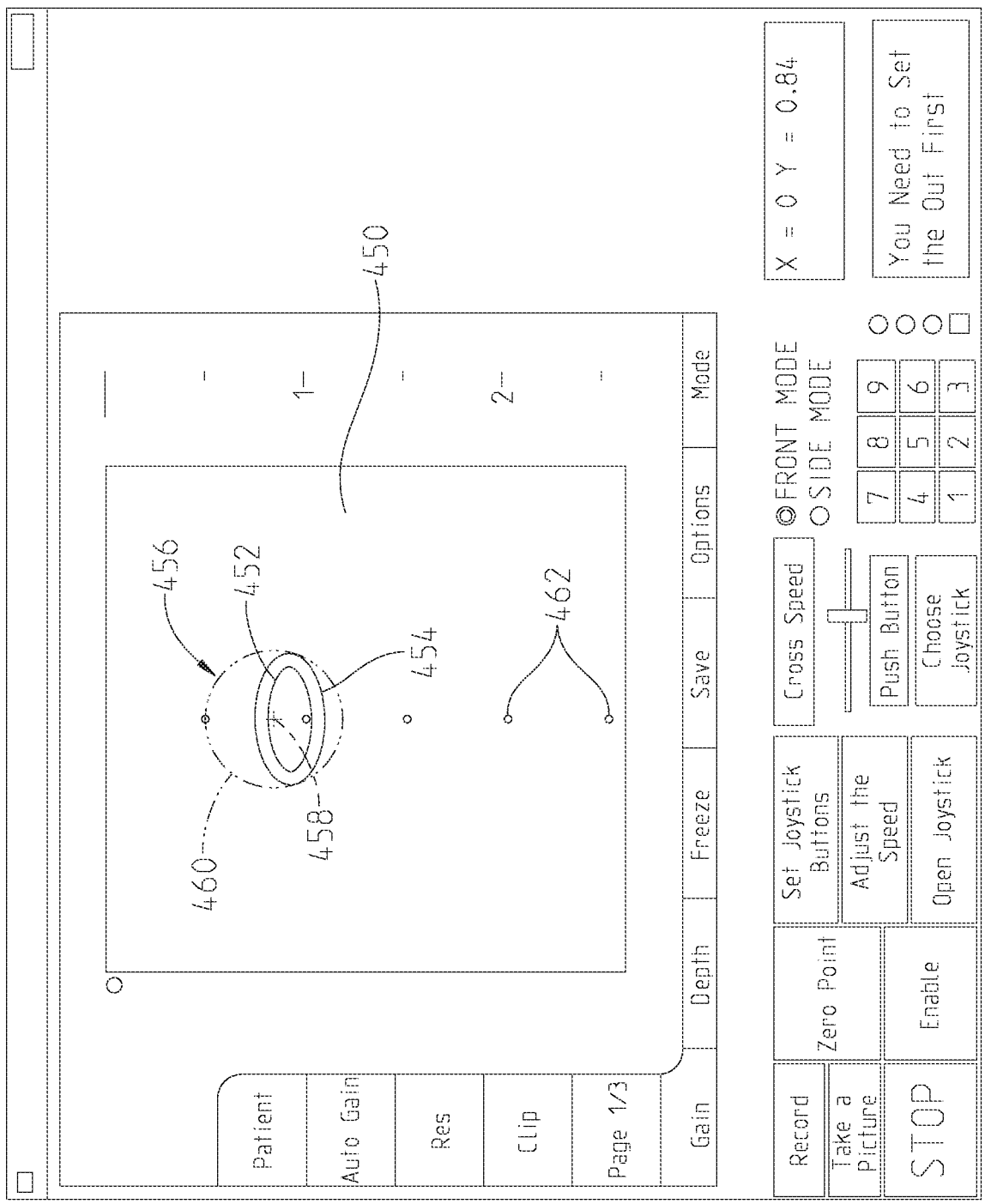
FIG. 33 is an illustrative view of the graphical user interface of FIG. 32, wherein the needle is entering into the vein.
Figure 34:
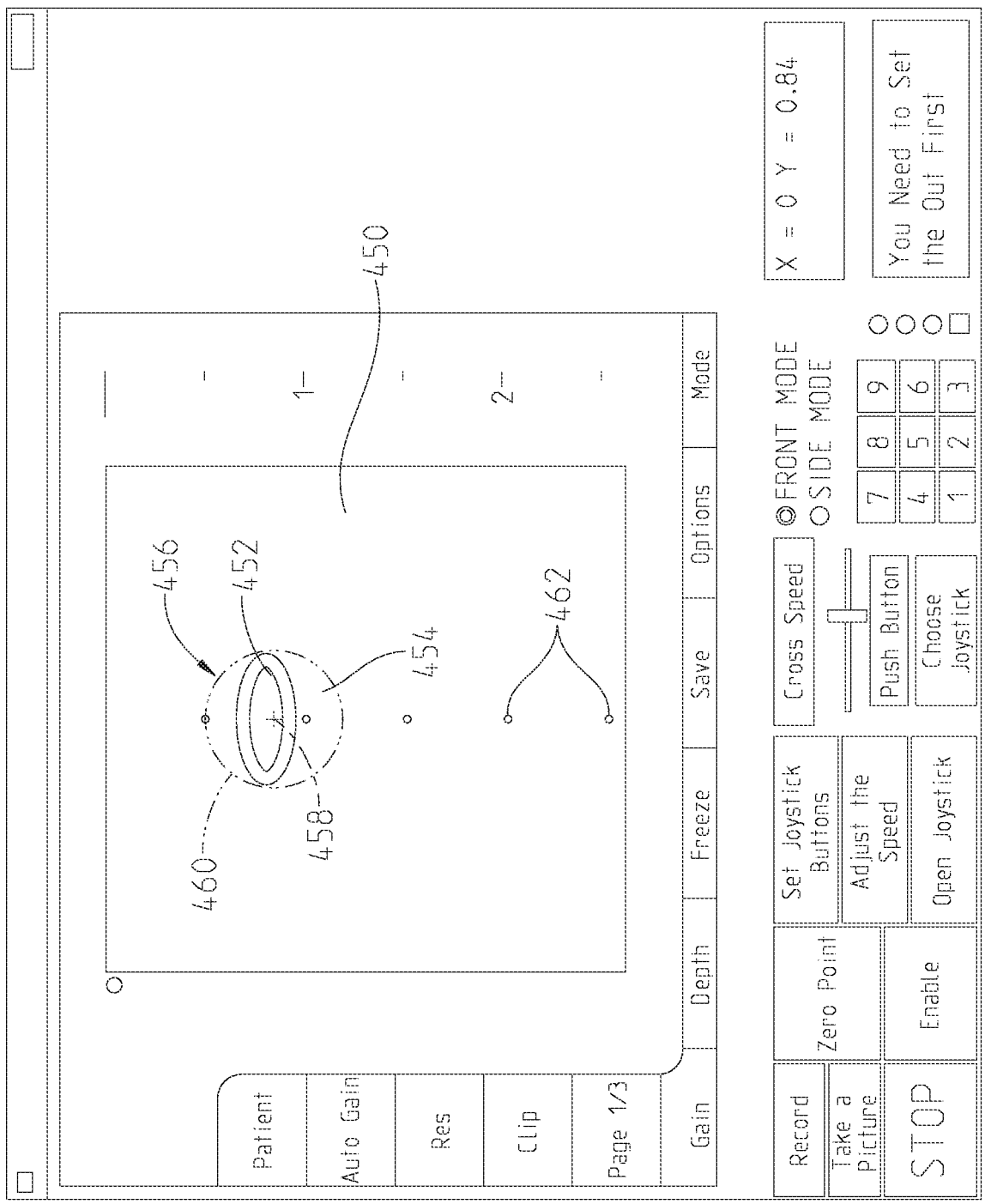
FIG. 34 is an illustrative view of the graphical user interface of FIG. 33, wherein the needle is inside the vein.

Ultrasound snapshots as displayed on the graphical user interface 150 of the needle insertion process are shown in FIGS. 32-34. As noted above, FIG. 27 illustrates the needle target 456 marking the target vein 60. FIG. 33 illustrates the needle 78 entering the target vein 60 as the motor 104 moves the needle assembly downwardly. FIG. 29 illustrates the needle 78 inside the target vein 60.

As disclosed above, the path planner module illustratively estimates the optimum trajectory based on the geometry of the dispenser and control unit (DCU) 16 and the needle 78 employed. It may be appreciated that this geometry may vary based upon the dimensions and positioning of the various components.

Figure 35:
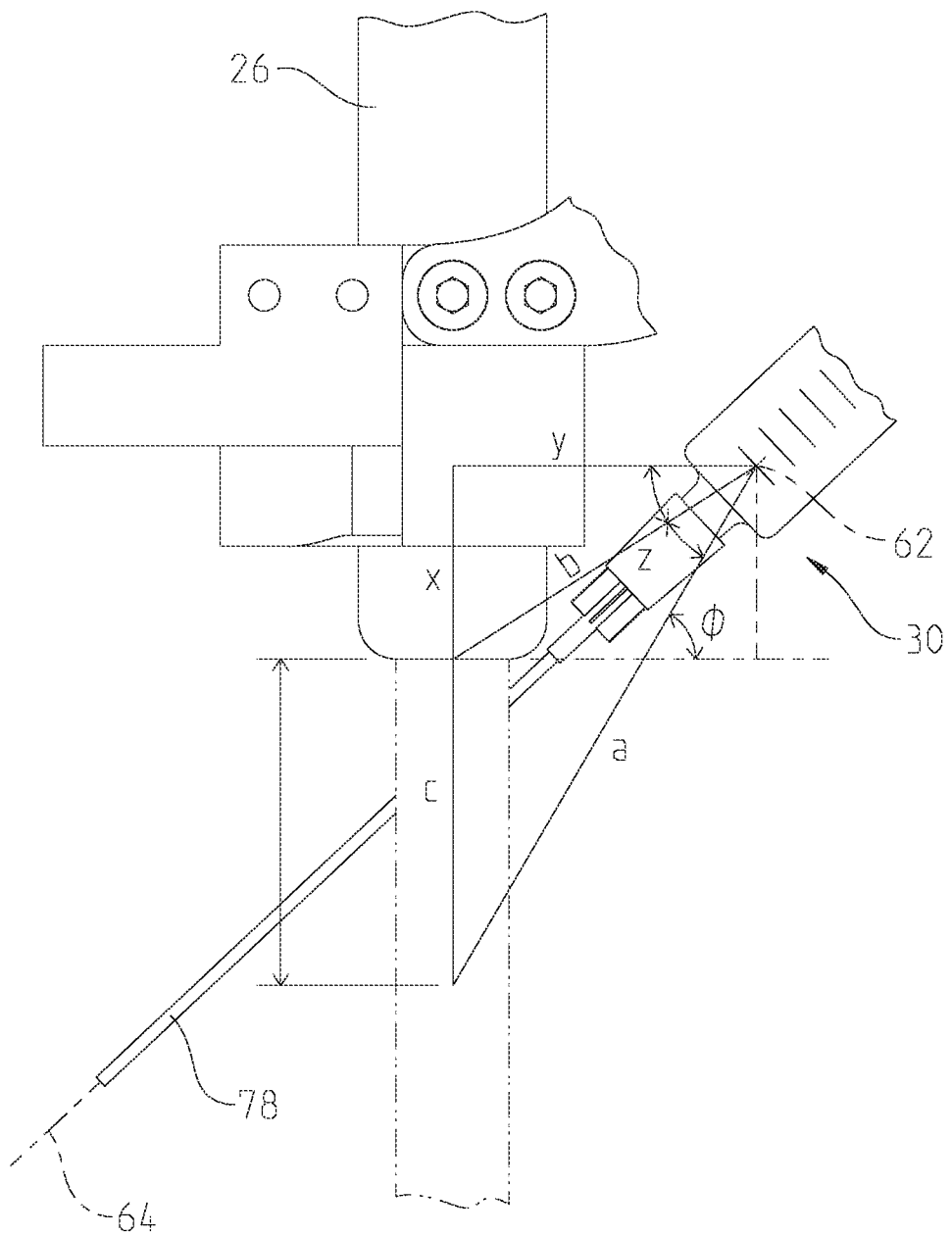
FIG. 35 is a detail view of the delivery system of FIG. 4, in partial schematic, showing illustrative geometry associated with the needle assembly.

With reference to FIG. 35, in one illustrative embodiment, the path of the needle 78 may be determined in the following manner. Given the dimension "c" is the penetration depth of the ultrasound, that "x" and "y" are the vertical and horizontal offsets between the ultrasound probe 26 and the axis 62 of the needle assembly 30, and that z is the needle offset between the ultrasound probe 26 and the axis 62 of the needle assembly 30, then the needle penetration "a" may be estimated as:

$$Q = y + z$$

$$a^2 = (c+x)^2 + Q^2$$

The angle phi $\Phi$ may then be calculated as:

$$\Phi = a\tan g((c+x)/Q)$$

Calibration is attained by either using the geometric information or using least mean square to fit the motor position to a polynom of second or higher order. Before use the system 10 is homed to a preset position.

For example, after calibration the motor angular increments (inc_r) can be calculated as:

$$\text{inc\_r} = a\tan g(k1/(k2+c)*k3$$

where k1 and k2 are fitting parameters and k3 is an scale constant.

The increments of the linear motor (inc_l) may be calculated as:

$$\text{inc\_l} = w1*c + w2$$

where w1 and w2 are fitting parameters.

Once the optimal trajectory is set, the optimal needle trajectory may be displayed on the window area 450 along with the needle trajectory.

The system 10 of the present disclosure may be used in a wide variety of applications that may be quite different in purpose but substantially identical in application of the concept. For example, the system 10 may be used in connection with the following illustrative applications: vascular access, tissue biopsy, lesion ablation, interventional cardiology, brachytherapy, joint injections, tendon sheath injections, injections of Dupuytren's cords, nerve blocks, spinal taps, abscess drainage, and chest tube placement.

One illustrative application is access to the vascular system through percutaneous puncture of a central artery or vein. The application of endovascular techniques has exploded in many specialties in pediatric and adult medicine including cardiology, interventional radiology, and vascular surgery. The initial step in every application is to introduce a needle into a vascular structure for subsequent insertion of wires, catheters, and devices. Accessing the vessel can be time consuming, dangerous and at times, impossible. Current practice involves either blind attempts based on the experience of the practitioner and knowledge of the anatomy or, increasingly, ultrasound guidance is used to facilitate the trial and error approach.

Another illustrative application is percutaneous biopsy and/or destruction of solid organ lesions. Examples of this need include liver lesions, lung lesions, kidney lesions and, most commonly, breast lesions. The problems are the same as listed above with the additional risk that inaccurate biopsy could result in a false negative assessment of the target lesion or ineffective destruction of malignant tissue.

A further illustrative application is spinal anesthesia, which is generally employed to inject medicine into the fluid of the patient's spinal cord. This is usually done only once, so there is no need to have a catheter placed.

Another illustrative application is epidural anesthesia, which involves injecting medicine just outside of the sac of fluid around your spinal cord (epidural space). A catheter is often left in place.

A further illustrative application is percutaneous drainage of intra-abdominal or intrathoracic abscesses or fluid collections for diagnosis and treatment.

With the illustrative system 10, a needle 78 may be autonomously directed to a target lesion with higher accuracy and precision than when guided by the human hand.

In connection with illustrative hand applications of the system 10, such as joint applications, tendon sheath injections and injections of Dupuytren's cords, it remains important to accurately place the needle 78. A potential risk of injection at the wrong site is tendon rupture. For this type of application, the following procedure may be performed.

A three dimensional model of the hand is illustratively constructed. This may be performed by scanning the hand using either stereo cameras, a laser scanner, structural light, or a combination thereof. An ultrasound scan is then performed. The three dimensional model is then used to determine the position of the fingers and register the ultrascan information. Next, a three dimensional model of the hand is displayed on a monitor and the tendon and cord areas are marked. The operator marks in the display the points to be injected and the amounts to be delivered. Alternatively, an automatic planner could search the optimal delivery strategy. After the injection points are defined, the trajectory of the delivery system is planned. Finally, the needle delivery system is activated.

Although the invention has been described in detail with reference to certain preferred embodiments, variations and modifications exist within the spirit and scope of the invention as described and defined in the following claims.

The invention claimed is:

1. An image guided autonomous needle insertion system comprising:
    an ultrasound probe;
    a mount coupled to the ultrasound probe;
    a needle assembly supported by the mount and configured to move with the ultrasonic probe, the needle assembly including a needle having first and second degrees of freedom relative to the mount and the ultrasound probe, the needle extending along a longitudinal axis;
    a first actuator configured to move the needle within a first degree of freedom, a second actuator configured to move the needle within a second degree of freedom, a first position sensor operably coupled to the first actuator, and a second position sensor operably coupled to the second actuator;
    a human machine interface operably coupled to the first and second actuators;
    wherein the first actuator is configured to rotate the needle assembly about an x-axis extending perpendicular to the longitudinal axis of the needle to align the needle with a target body site and defining the first degree of freedom, and the first position sensor is configured to detect the position of the needle assembly about the x-axis;
    wherein the second actuator is configured to translate the needle assembly along a z-axis extending parallel to the longitudinal axis of the needle to move the needle into and out of the target body site and defining the second degree of freedom, and the second position sensor is configured to detect the position of the needle assembly along the z-axis;
    a frame grabber in communication with the ultrasound probe configured for capturing an ultrasound image from the ultrasound probe;
    an image processor in communication with the frame grabber configured for analyzing the ultrasound image;
    a path planner configured to determine a desired path for the needle, the path planner including a needle detection and tracking module, and a target detection and tracking module;
    the needle detection and tracking module configured to receive information from the first position sensor regarding the position of the needle assembly about the x-axis, and from the second position sensor regarding the position of the needle assembly along the z-axis; and
    the target detection and tracking module configured to receive information from the image processor to determine a global position of the target body site;
    wherein the desired path for the needle is determined based on the position of the needle assembly about the x-axis, the position of the needle assembly about the z-axis and the global positon of the target body site.

2. The insertion system of claim 1, wherein the human machine interface includes a graphical user interface having a command window.

3. The insertion system of claim 2, wherein the human machine interface includes a joystick coupled to the ultrasound probe and configured to move with the ultrasound probe.

4. The insertion system of claim 3, wherein the joystick includes a chamber receiving an upper end of the ultrasound probe.

5. The insertion system of claim 2, wherein the command window includes an ultrasound window area having representations of the target body site, a longitudinal axis of the ultrasound probe, and a needle mark.

6. The insertion system of claim 5, wherein:
    the ultrasound probe is configured to be mounted within a dispenser and control unit and
    the dispenser and control unit is configured for manual manipulation to align the target body site with the longitudinal axis of the ultrasound probe, and the first actuator is configured to align the needle mark with the target body site.

7. The insertion system of claim 1, wherein:
    the ultrasound probe defines a longitudinal axis and is configured to be mounted within a dispenser and control unit in at least one of a front configuration and a side configuration, the ultrasound probe in the side configuration being positioned 90 degrees about the longitudinal axis from the front configuration; and
    the image processor is configurable by the user to account for the at least one front configuration and side configuration.

8. The insertion system of claim 1, further comprising a third actuator configured to move the needle within a third degree of freedom, and a third position sensor operably coupled to the third actuator, wherein the third actuator is configured to translate the needle assembly along the x-axis, and the third position sensor is configured to detect the position of the needle assembly along the x-axis.

9. The insertion system of claim 8, wherein the third actuator comprises an electrical motor.

10. The insertion system of claim 1, wherein the human machine interface includes a plurality of operator inputs, the operator inputs including a first directional input configured to cause the first actuator to move the needle assembly in a first direction within the first degree of freedom, a second directional input configured to cause the first actuator to move the needle assembly in a second direction within the first degree of freedom, a start input configured to cause the second actuator to move the needle assembly in a first direction within the second degree of freedom toward the target body site, and an out input configured to cause the second actuator to move the needle assembly in a second direction within the second degree of freedom away from the target body site.

11. The insertion system of claim 1, wherein the first actuator comprises a first electrical motor, and the second actuator comprises a second electrical motor.

12. The insertion system of claim 1, wherein the needle assembly includes five degrees of freedom.

13. An image guided autonomous needle insertion system comprising:
   an ultrasound probe;
   a mount coupled to the ultrasound probe;
   a needle assembly supported by the mount and configured to move with the ultrasonic probe, the needle assembly including a needle having first and second degrees of freedom relative to the mount and the ultrasound probe, the needle extending along a longitudinal axis;
   a first actuator configured to move the needle within a first degree of freedom, a second actuator configured to move the needle within a second degree of freedom, a first position sensor operably coupled to the first actuator, and a second position sensor operably coupled to the second actuator;
   a human machine interface operably coupled to the first and second actuators;
   wherein the first actuator is configured to rotate the needle assembly about an x-axis extending perpendicular to the longitudinal axis of the needle to align the needle with a target body site and defining the first degree of freedom, and the first position sensor is configured to detect the position of the needle assembly about the x-axis;
   wherein the second actuator is configured to translate the needle assembly along a z-axis extending parallel to the longitudinal axis of the needle to move the needle into and out of the target body site and defining the second degree of freedom, and the second position sensor is configured to detect the position of the needle assembly along the z-axis;
   a frame grabber in communication with the ultrasound probe;
   an image processor in communication with the frame grabber, the image processor including an image pre-processing module, and an image segmentation module;
   the image preprocessing module configured to remove noise from an ultrasound image received from the frame grabber, and calibrate the ultrasound image;
   the image segmentation module configured to decompose the ultrasound image into separate objects;
   a path planner configured to determine a desired path for the needle, the path planner including a needle detection and tracking module, and a target detection and tracking module;
   the needle detection and tracking module configured to receive information from the first and second position sensors to determine the relative position of the needle assembly; and
   the target detection and tracking module configured to receive information from the image processor to determine a global position of the target body site;
   wherein the desired path for the needle is determined based on the position of the needle assembly about the x-axis, the position of the needle assembly about the z-axis and the global positon of the target body site.

\* \* \* \* \*